(12) United States Patent
Craig et al.

(10) Patent No.: US 10,369,086 B2
(45) Date of Patent: Aug. 6, 2019

(54) COMPOSITE MATERIAL HAVING CERAMIC FIBERS

(71) Applicant: 3M INNOVATIVE PROPERTIES COMPANY, St. Paul, MN (US)

(72) Inventors: Bradley D. Craig, Lake Elmo, MN (US); Gregory A. Kobussen, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 136 days.

(21) Appl. No.: 15/552,751

(22) PCT Filed: Mar. 1, 2016

(86) PCT No.: PCT/US2016/020220
§ 371 (c)(1),
(2) Date: Aug. 22, 2017

(87) PCT Pub. No.: WO2016/140950
PCT Pub. Date: Sep. 9, 2016

(65) Prior Publication Data
US 2018/0028413 A1 Feb. 1, 2018

Related U.S. Application Data

(60) Provisional application No. 62/128,819, filed on Mar. 5, 2015.

(51) Int. Cl.
| | | |
|---|---|---|
| *A61K 6/08* | (2006.01) | |
| *A61K 6/02* | (2006.01) | |
| *A61K 6/00* | (2006.01) | |
| *A61K 6/083* | (2006.01) | |
| *C04B 35/80* | (2006.01) | |

(52) U.S. Cl.
CPC .......... *A61K 6/0205* (2013.01); *A61K 6/0005* (2013.01); *A61K 6/0008* (2013.01); *A61K 6/0017* (2013.01); *A61K 6/0073* (2013.01); *A61K 6/083* (2013.01); *C04B 35/806* (2013.01)

(58) Field of Classification Search
CPC .................................................. A61K 6/0008
See application file for complete search history.

(56) References Cited

U.S. PATENT DOCUMENTS

| | | | |
|---|---|---|---|
| 3,066,112 A | 11/1962 | Bowen | |
| 3,117,099 A | 1/1964 | Proops | |
| 3,539,533 A | 11/1970 | Lee, II | |
| 3,629,187 A | 12/1971 | Waller | |
| 3,708,296 A | 1/1973 | Schlesinger | |
| 3,709,866 A | 1/1973 | Waller | |
| 3,751,399 A | 8/1973 | Lee, Jr. | |
| 3,766,132 A | 10/1973 | Lee, Jr. | |
| 3,860,556 A | 1/1975 | Taylor | |
| 4,002,669 A | 1/1977 | Gross | |
| 4,069,055 A | 1/1978 | Crivello | |
| 4,115,346 A | 9/1978 | Gross | |
| 4,216,288 A | 8/1980 | Crivello | |
| 4,250,311 A | 2/1981 | Crivello | |
| 4,259,117 A | 3/1981 | Yamauchi | |
| 4,292,029 A | 9/1981 | Craig | |
| 4,298,738 A | 11/1981 | Lechtken | |
| 4,308,190 A | 12/1981 | Walkowiak | |
| 4,324,744 A | 4/1982 | Lechtken | |
| 4,327,014 A | 4/1982 | Kawahara | |
| 4,356,296 A | 10/1982 | Griffith | |
| 4,379,695 A | 4/1983 | Orlowski | |
| 4,385,109 A | 5/1983 | Lechtken | |
| 4,387,240 A | 6/1983 | Berg | |
| 4,404,150 A | 9/1983 | Tsunekawa | |
| 4,503,169 A | 3/1985 | Randklev | |
| 4,642,126 A | 2/1987 | Zador | |
| 4,648,843 A | 3/1987 | Mitra | |

(Continued)

FOREIGN PATENT DOCUMENTS

| | | |
|---|---|---|
| EP | 0173567 | 3/1986 |
| EP | 0201031 | 11/1986 |

(Continued)

OTHER PUBLICATIONS

Adamson, "Aminoalkyl tertiary carbinols and derived products. Part I. 3-Amino-1 : 1-diphenylpropan-1-ols",J. Chem. Soc.; 1949; pp. S144-S152.
Klapdohr, "New Inorganic Components for Dental Filing Composites", Monatshefte fur chemie, 2005, vol. 136, pp. 21-45 (XP01937868).
International search report for PCT International Application No. PCT/US2016/020220 dated May 9, 2016, 5 pages.

*Primary Examiner* — Michael F Pepitone

(57) ABSTRACT

The present disclosure provides a composite material, a method of making and using the composite material and dental products made by hardening the composite material. The composite material includes a polymerizable component, ceramic fibers and nanoclusters. Each of the ceramic fibers of the composite material has a length and where the length of fifty percent of the ceramic fibers, based on a total number of the ceramic fibers, is at least 50 micrometers and the length of ninety percent of the ceramic fibers, based on the total number of the ceramic fibers, is no greater than 500 micrometers. The composite material can also include discrete non-fumed metal oxide nanoparticles. The composite material can be hardened to become any one of a dental restorative, a dental adhesive, a dental mill blank, a dental cement, a dental prostheses, an orthodontic device, an orthodontic adhesive, a dental casting material or a dental coating.

28 Claims, No Drawings

(56) References Cited

U.S. PATENT DOCUMENTS

| | | | |
|---|---|---|---|
| 4,652,274 A | 3/1987 | Boettcher | |
| 4,695,251 A | 9/1987 | Randklev | |
| 4,710,523 A | 12/1987 | Lechtken | |
| 4,737,593 A | 4/1988 | Ellrich | |
| 4,985,340 A | 1/1991 | Palazzotto | |
| 5,076,844 A | 12/1991 | Fock | |
| 5,084,586 A | 1/1992 | Farooq | |
| 5,089,536 A | 2/1992 | Palazzotto | |
| 5,124,417 A | 6/1992 | Farooq | |
| 5,266,609 A * | 11/1993 | Hall | A61K 6/0023 523/116 |
| 5,425,640 A * | 6/1995 | Scharf | A61C 5/007 427/299 |
| 5,545,676 A | 8/1996 | Palazzotto | |
| 5,856,373 A | 1/1999 | Kaisaki | |
| 5,998,549 A | 12/1999 | Milbourn | |
| 6,025,406 A | 2/2000 | Oxman | |
| 6,030,606 A | 2/2000 | Holmes | |
| 6,251,963 B1 | 6/2001 | Kohler | |
| 6,306,926 B1 | 10/2001 | Bretscher | |
| 6,376,590 B2 | 4/2002 | Kolb | |
| 6,387,981 B1 | 5/2002 | Zhang | |
| 6,572,693 B1 | 6/2003 | Wu | |
| 6,624,211 B2 | 9/2003 | Karim | |
| 6,730,156 B1 * | 5/2004 | Windisch | A61K 6/0017 106/35 |
| 6,765,036 B2 | 7/2004 | Dede | |
| 6,872,076 B2 * | 3/2005 | Karmaker | A61K 6/0073 433/201.1 |
| 6,899,948 B2 | 5/2005 | Zhang | |
| 7,022,173 B2 | 4/2006 | Cummings | |
| 7,030,049 B2 | 4/2006 | Rusin | |
| 7,085,063 B2 | 8/2006 | Magarill | |
| 7,090,721 B2 | 8/2006 | Craig | |
| 7,090,722 B2 | 8/2006 | Budd | |
| 7,156,911 B2 | 1/2007 | Kangas | |
| 7,160,528 B2 | 1/2007 | Rusin | |
| 7,361,216 B2 | 4/2008 | Kangas | |
| 7,393,882 B2 | 7/2008 | Wu | |
| 7,429,422 B2 | 9/2008 | Davidson | |
| 7,649,029 B2 | 1/2010 | Kolb | |
| 8,647,510 B2 | 2/2014 | Kolb | |
| 2008/0160206 A1 * | 7/2008 | Burtscher | A61K 6/0073 427/450 |
| 2010/0089286 A1 | 4/2010 | Craig | |
| 2011/0171609 A1 | 7/2011 | Yang | |
| 2011/0196062 A1 | 8/2011 | Craig | |
| 2013/0023600 A1 | 1/2013 | Kobashigawa | |

FOREIGN PATENT DOCUMENTS

| | | |
|---|---|---|
| EP | 0201778 | 11/1986 |
| EP | 0373384 | 3/1994 |
| GB | 2291053 | 1/1996 |
| WO | WO 1999-047104 | 9/1999 |
| WO | WO 2000-038619 | 7/2000 |
| WO | WO 2000-042092 | 7/2000 |
| WO | WO 2001-007444 | 2/2001 |
| WO | WO 2001-092271 | 12/2001 |
| WO | WO 2003-063804 | 8/2003 |
| WO | WO 2006-020760 | 2/2006 |
| WO | WO 2008-000917 | 1/2008 |

* cited by examiner

COMPOSITE MATERIAL HAVING CERAMIC FIBERS

TECHNICAL FIELD

The present disclosure provides for a composite material, and more particularly a composite material having ceramic fibers.

BACKGROUND

Direct dental restorative materials consist of a curable phase, typically a methacrylate resin, an initiator and a filler system. These materials are typically highly filled with particulate such as nanoscale particles, micrometer milled materials and/or solution grown inorganics. Furthermore, similar compositions made from pre-cured "composites" (e.g., dental mill blanks) have been introduced to the market, where the material is cured out of the mouth and shaped into a final restorative shape (e.g., inlay, onlay or crown) via a reduction process (e.g., milling). All of these dental restorative materials have requirements that include high strength, stiffness, and fracture toughness to function in the oral environment. Especially in large posterior restorations, a higher fracture toughness material is highly desirable.

Attempts have been made to include fibers in dental restorative materials in order to improve their mechanical properties. However, this has come at a cost to handling and aesthetic characteristics. The use of fibers unfortunately creates a stiff, "crunchy" type of handling that is difficult to work with (e.g., shape, and feather). Once cured, the surfaces of these dental restorative materials rapidly lose their gloss with every day wear. Additionally, many of these dental restorative materials produce a highly opaque material due to refractive index mismatch between the fiber and the resin. This refractive index mismatch results in a less than desirable aesthetic result.

As such, there is a need in the art for a composite material that includes fibers, where the composite material is easy to handle and provides good aesthetics properties while still providing the necessary mechanical properties for use as a dental restorative material.

SUMMARY

The present disclosure provides a composite material having improved handling properties along with good aesthetic qualities while still providing the necessary mechanical properties for use as a dental restorative material. Specifically, the composite material includes 20 to 40 weight percent (wt. %) of a polymerizable component; 4 to 50 wt. % of ceramic fibers; and 20 to 70 wt. % of nanoclusters, where the wt. % values of the composite material are based on a total weight of the composite material and total to a value of 100 wt. %. Each of the ceramic fibers has a length, where the length of fifty percent of the ceramic fibers, based on a total number of the ceramic fibers, is at least 50 micrometers and the length of ninety percent of the ceramic fibers, based on the total number of the ceramic fibers, is no greater than 500 micrometers. The highly uniform length of the ceramic fibers along with the nanoclusters surprisingly results in improvements to both the handling properties of the composite material and upon hardening the mechanical properties of the hardened composite material. In addition, the aesthetic properties achieved by the composite material allow for, among other things, a polish on a surface of the composite material to be retained even after repetitive abrasive contact.

The composite material can include up to 12 wt. % of nanoparticles based on the total weight of the composite material. For example, the composite material can include 2 to 12 wt. % of nanoparticles based on the total weight of the composite material. The nanoparticles can be discrete non-fumed metal oxide nanoparticles. Discrete non-fumed metal oxide nanoparticles can be discrete non-fumed heavy metal oxide nanoparticles. The discrete non-fumed metal oxide nanoparticles can also include both discrete non-fumed heavy metal oxide nanoparticles and discrete non-fumed non-heavy metal oxide nanoparticles. The composite material can also include 22 to 64 wt. % of nanoclusters, as discussed herein.

A variety of physical properties are possible for the ceramic fibers of the present disclosure. For example, the length of sixty-five percent of the ceramic fibers, based on a total number of the ceramic fibers, can be at least 100 micrometers and the length of ninety percent of the ceramic fibers, based on the total number of the ceramic fibers, can be no greater than 350 micrometers. The ceramic fibers can have an arithmetic mean length of 50 micrometers to 500 micrometers, preferably the ceramic fibers can have an arithmetic mean length of 100 micrometers to 170 micrometers. The ceramic fibers can also have an arithmetic mean diameter of 0.5 to 20 micrometers. In one embodiment, the arithmetic mean diameter of the ceramic fibers can be 9 to 12 micrometers.

The ceramic fibers can be amorphous ceramic fibers. In one embodiment, the ceramic fibers are formed with aluminum oxide and silicon dioxide and have less than 14 weight percent of boron trioxide based on the total weight of the ceramic fibers. Examples, of such ceramic fibers can have a surface area of at least 10 square meters per gram ($m^2/g$).

The polymerizable component of the composite material can form a hardened polymerizable component having a refractive index. As discussed herein, the refractive index of the hardened polymerizable component is closely matched to the refractive index of the ceramic fibers. For example, the ceramic fibers can have a refractive index value within 0.1 or less of the refractive index of the hardened polymerizable component. In an additional embodiment, the polymerizable component can form a hardened polymerizable component having a refractive index, where the ceramic fibers have a refractive index value within 0.05 or less of the refractive index of the hardened polymerizable component. Examples of refractive index values for the ceramic fibers include ceramic fibers have a refractive index value of 1.40 to 1.65. In an additional example, the refractive index value of the ceramic fibers is 1.50 to 1.58.

For the various embodiments, the polymerizable component can be an ethylenically unsaturated compound. The polymerizable component can further include an initiator selected from the group consisting of a free radical initiator, a photoinitiator, a thermally activated initiator or a combination thereof.

The composite material of the present disclosure can be hardened to make a dental product. The dental product can be selected from the group consisting of a dental restorative, a dental adhesive, a dental mill blank, a dental cement, a dental prostheses, an orthodontic device, an orthodontic adhesive, a dental casting material, artificial crowns, anterior fillings, posterior fillings, and cavity liners or a dental coating. The composite material of the present disclosure can also be used near or on a tooth surface. For example, the composite material can be placed near or on a tooth surface, where the shape of the composite material near or on the tooth surface can be changed prior to hardening the composite material. Changing the shape of the composite material near or on the tooth surface can include shaping the composite material into a dental product selected from the group consisting of a dental prosthesis, an orthodontic device, a dental crown, an anterior filling, a posterior filing or a cavity liner. After hardening, the composite material can be polished.

The nanoclusters of the composite material can be silica-zirconia nanoclusters. Examples of such silica-zirconia nanoclusters include those formed by primary particles, where each of the primary particles has a diameter of 1 nanometer to 200 nanometers, where the primary particles forming the silica-zirconia nanocluster are grouped together in a cluster formation. Such nanoclusters may be substantially amorphous. Such nanoclusters may contain crystalline phases (e.g., zirconia) within them.

The present disclosure further includes a method of making the composite material, where the method includes providing 20 to 40 wt. % of the polymerizable component, providing 4 to 50 wt. % of ceramic fibers, and providing 20 to 70 wt. % of nanoclusters, where the wt. % values of the composite material are based on a total weight of the composite material and total to a value of 100 wt. %, where each of the ceramic fibers has a length and where the length of fifty percent of the ceramic fibers, based on a total number of the ceramic fibers, is at least 50 micrometers and the length of ninety percent of the ceramic fibers, based on the total number of the ceramic fibers, is no greater than 500 micrometers; and admixing the polymerizable component, the ceramic fibers and the nanoclusters to make the composite material. The method can also include providing up to 12 wt. % of nanoparticles based on the total weight of the composite material, and admixing the polymerizable component, the ceramic fibers and the nanoclusters and the nanoparticles to make the composite material.

The ceramic fibers of the present disclosure can also be treated in order to modify their surface properties. For example, the ceramic fibers can include a surface area, where the method includes treating the ceramic fibers to change the surface area of the ceramic fibers. So, for example, the ceramic fibers can include a predetermined amount of boron trioxide where treating the ceramic fibers to change the surface area of the ceramic fibers includes removing at least a portion of the boron trioxide from the ceramic fibers. Removing at least a portion of the boron trioxide can include boiling the ceramic fibers in water to remove the boron trioxide in the ceramic fibers.

The present disclosure further includes a method of using the composite material of the present disclosure, where the method includes placing the composite material of the present disclosure near or on a tooth surface; changing the shape of the composite material near or on the tooth surface; and hardening the composite material. Finally, the present disclosure provides a kit that includes the composite material as provided herein and at least one container to hold the composite material.

DETAILED DESCRIPTION

The present disclosure provides a composite material having improved handling properties along with good aesthetic qualities while still providing the necessary mechanical properties for use as a dental restorative material. Specifically, the composite material includes a polymerizable component, ceramic fibers and nanoclusters. The ceramic fibers used in the composite material, as discussed herein, have a highly uniform length. The highly uniform length of the ceramic fibers along with the use of the nanoclusters surprisingly results in improvements to both the handling properties of the composite material and upon hardening the aesthetics properties of the hardened composite material. Examples of such improved aesthetics properties include hardened composite materials that are able to retain their polish even after exposure to repetitive abrasion, such as through brushing with toothpaste.

The hardened composite material of the present disclosure may also have other desirable aesthetic, physical and mechanical properties. For example, the hardened composite material of the present disclosure can have radiopacity, high mechanical strength and a substantial translucency. Radiopacity is a very desirable property for a composite material used in dental applications. Being radiopaque allows the composite material to be examined using standard dental X-ray equipment, thereby facilitating long term detection of marginal leakage or caries in tooth tissue adjacent to the hardened composite material.

The hardened composite material can have a substantial translucency (e.g., a low visual opacity) to visible light. Having translucency is desirable so that the hardened composite material will have a life-like appearance when used as a dental restorative material. If such a composite material is intended to be hardened or polymerized using visible light-induced photoinitiation, translucency is desirable in order to reach the depth of cure required (sometimes as much as two millimeters or more), to accomplish uniform hardness in the hardened composite material, and to respond to the physical limitations imposed by carrying out the hardening reaction within the mouth (which require, among other things, that the unhardened composite material usually be exposed to light from limited angles, and that the hardening radiation be provided by a portable instrument). The translucency can be achieved for the composite material, as discussed herein, in part by matching the refractive index of the ceramic fibers with the refractive index of the hardened polymerizable component of the composite material.

Practitioners also desire good handling properties in a composite material used for dental applications, as this property translates to time savings. For example, in dental restorative work, it is desirable that the composite material be easily shaped, contoured and feathered into the desired shape. Until the present disclosure, attempts at using fibers in composite materials at loadings levels sufficient to improve the mechanical properties made the handling of the composite material poor at best. Such attempts with ground or milled fibers created a "crunchy" type of handling, which is something to avoid for a dental restorative material to have good handling and "featherability" characteristics. These other composite materials also had "lumps," which makes for unpredictable and non-uniform handling of the material.

Unlike these failed attempts, the composite material of the present disclosure maintains good handling characteristics at fiber loadings sufficient to improve the mechanical properties. The composite material of the present disclosure displays a consistent and uniform composition, which allows for predictable and uniform handling of the composite material. In addition, the refractive index of the ceramic fibers and the polymerizable component used in the present disclosure are suitably matched so as to provide substantial translucency (e.g., low visual opacity) and high aesthetic quality for use as a dental restorative material. Finally, the hardened composite material of the present disclosure displays enhanced fracture toughness and flexural modulus due to the presence of the ceramic fibers and the nanoclusters, with minimal degradation of handling or aesthetic properties of the composite material. This is unexpected, as the use of fibers is known to decrease both handling and aesthetic properties of composite materials.

While not wishing to be bound by theory, it is hypothesized that it is a combination of the size and relatively uniform distribution of the ceramic fibers and the nanoclusters used in the composite material of the present disclosure that is leading to these favorable attributes. The highly uniform length of the ceramic fibers surprisingly results in improvements to both the handling properties of the composite material and upon hardening the physical properties of the hardened composite material. Examples of such improved physical properties include dental restorative materials that are able to retain their polish after repetitive abrasive contact.

Definitions

As used herein, a "ceramic" is a rigid material that consists of an infinite three-dimensional network comprising metals bonded to carbon, nitrogen or oxygen. The ceramic, as used herein, may be crystalline, partially crystalline or amorphous.

The term "electron donor" generally refers to a compound that has a substituent that can donate electrons. Suitable examples include, but are not limited to, a primary amino, secondary amino, tertiary amino, hydroxy, alkoxy, aryloxy, alkyl, or combinations thereof.

As used herein, "hardenable" is descriptive of a material or composition that can be cured (e.g., polymerized or crosslinked) or solidified, for example, by removing solvent (e.g., by evaporation and/or heating); heating to induce polymerization and/or crosslinking; irradiating to induce polymerization and/or crosslinking; and/or by mixing one or more components to induce polymerization and/or crosslinking.

By "dental product" is meant an article that can be adhered (e.g., bonded) to an oral surface (e.g., a tooth structure). Typically, a dental product is a restored dentition or a portion thereof. Examples include restoratives, replacements, inlays, onlays, veneers, full and partial crowns, bridges, implants, implant abutments, copings, anterior fillings, posterior fillings, cavity liners, sealants, dentures, posts, bridge frameworks and other bridge structures, abutments, orthodontic appliances and devices, and prostheses (e.g., partial or full dentures).

As used herein, "sizing" is defined as starch, oil, wax or other suitable ingredients (e.g., an organic ingredient) applied to a fiber strand to protect and aid handling. A sizing contains ingredients to provide lubricity and binding action. Sizing may also encompass surface treatments, for example with a silane, where the silane may include a reactive group, for example a polymerizable group.

By "oral surface" is meant a soft or hard surface in the oral environment. Hard surfaces typically include tooth structure including, for example, natural and artificial tooth surfaces, bone, tooth models, dentin, enamel, cementum, and the like By "filler" is meant a particulate material suitable for use in the oral environment. Dental fillers generally have a number average particle size diameter of at most 100 micrometers.

By "contouring" refers to the process of shaping a material (using dental instruments) so that it resembles the natural dental anatomy. For easy contouring, materials should have a sufficiently high viscosity that they maintain their shape after manipulation with a dental instrument, and yet the viscosity should not be so high that it is difficult to shape the material.

By "feathering" refers to the process of reducing the dental restorative material to a thin film in order to blend the material into the natural dentition. This is done with a dental instrument at the margin of the manipulated material and the natural dentition.

By "amorphous ceramic fibers" is meant a non-crystalline solid that lacks the long-range order characteristic of a crystal. As used herein, "amorphous ceramic fibers" are synonymous with glass.

As used herein, "nanoparticles" are discrete non-fumed metal oxide nanoparticles. Discrete non-fumed metal oxide nanoparticles can be further classified as either "discrete non-fumed non-heavy metal oxide nanoparticles" or "discrete non-fumed heavy metal oxide nanoparticles." The "discrete non-fumed non-heavy metal oxide nanoparticles" means an oxide of elements other than those of heavy metals (which are defined herein as the "discrete non-fumed heavy metal oxide nanoparticles"). As used herein, "non-heavy metal oxide" means a metal oxide of elements having an atomic number of no greater than 28. In one aspect of the disclosure, silica is an example of a non-heavy metal oxide and silica nanoparticles are an example of discrete non-fumed non-heavy metal oxide nanoparticles. As used herein, "heavy metal oxide" means an oxide of elements having an atomic number greater than 28. In one aspect of the disclosure, zirconium oxide is an example of the heavy metal oxide.

The average particle size of nanoparticles can be determined by cutting a thin sample of hardened dental composition and measuring the particle diameter of about 50-100 particles using a transmission electron micrograph at a magnification of 300,000 and calculating the average.

As used herein, "discrete" means unaggregated, individual particles (e.g. nanoparticles) that are separate from each other.

As used herein, a "nanocluster" generally refers to a group of two or more nanoparticles associated by relatively weak, but sufficient intermolecular forces that cause the nanoparticles to clump to together, even when dispersed in a hardenable resin. Preferred nanoclusters can comprise loosely aggregated substantially amorphous cluster of discrete non-fumed non-heavy metal oxide nanoparticles (e.g., silica nanoparticles) and heavy metal oxide (e.g., zirconia). Where zirconia is present as the heavy metal oxide, the zirconia can be crystalline or amorphous. Furthermore, the heavy metal oxide can be present as particles (e.g., discrete non-fumed heavy metal oxide nanoparticles such as zirconia nanoparticles). The particles from which the nanocluster is formed preferably have an average diameter of 5 nm to about 100 nm. However, the average particle size of the loosely aggregated nanocluster is typically considerably larger. Typically, the nanoclusters have a longest dimension in the micrometer range (e.g., 3 micrometers, 5 micrometers, 7 micrometers, 10 micrometers, and in some cases, 30 to 50 micrometers). Nanocluster size may be determined according to the methods generally described in U.S. Pat. No. 6,730,156 (column 21, lines 1-22, "Cluster Size Determination").

By "substantially amorphous" it is meant that the nanoclusters are essentially free of crystalline structure. Absence of crystallinity (or presence of amorphous phases) is preferably determined by a procedure that provides a Crystallinity Index, as generally described in U.S. Pat. No. 6,730,156 (column 21, lines 23 to column 22, line 33, "Crystallinity Index Procedure"). The Crystallinity Index characterizes the extent a material is crystalline or amorphous, whereby a value of 1.0 is indicative of a fully crystalline structure, and a value near zero indicates presence of amorphous phase only. The nanoclusters of the present disclosure preferably have an index of less than about 0.1; more preferably less than about 0.05.

By "nano" is meant a material in a form having at least one dimension that is, on average, at most 200 nanometers (e.g., discrete non-fumed metal oxide nanoparticles). Thus, nano materials refer to materials including, for example, nanoparticles and nanoclusters, as defined herein. So, for example, "nanoparticles" refers to particles having a number average diameter of at most 200 nanometers. As used herein for a spherical particle, "size" refers to the diameter of the particle. As used herein for a non-spherical particle, "size" refers to the longest dimension of the particle. In certain embodiments, the nanoparticles are comprised of discrete, non-aggregated and non-agglomerated particles.

As used herein, the term "ethylenically unsaturated compound" is meant to include monomers, oligomers, and polymers having at least one ethylenic unsaturation.

By "polymerization" is meant the forming of a higher weight material from monomers or oligomers. The polymerization reaction also can involve a cross-linking reaction.

As used herein, the term "(meth)acrylate" is a shorthand reference to acrylate, methacrylate, or combinations thereof, and "(meth)acrylic" is a shorthand reference to acrylic, methacrylic, or combinations thereof. As used herein, "(meth)acrylate-functional compounds" are compounds that include, among other things, a (meth)acrylate moiety.

As used herein a "hardened composite material" is the composite material of the present disclosure that has undergone a physical and/or a chemical transformation to produce a solid and firm composite material that is resistant to pressure. The physical and/or chemical transformation of the composite material can be due to a setting, curing, polymerizing, crosslinking or a fusing process.

As used herein "translucency" is the degree to which a material transmits light. This may be quantified by contrast ratio, translucency parameter, or percent transmittance through a known thickness of material. Translucency in dental restorative materials is often determined from the contrast ratio. The contrast ratio is the ratio of white light remission from a specimen placed over a standardized black background ($R_b$) and a standardized white background ($R_w$). The contrast ratio is calculated as $CR=R_b/R_w \times 100$. A contrast ratio of 100 represents a completely opaque specimen. Translucency is expressed as 100−CR.

As used herein a "dental mill blank" is a block of material (e.g., hardened composite material) from which dental product can be milled.

By "machining" is meant milling, grinding, cutting, carving, or shaping a material having a three dimensional structure or shape by a machine.

The term "comprising" and variations thereof (e.g., comprises, includes, etc.) do not have a limiting meaning where these terms appear in the description and claims.

As used herein, "CAD/CAM" is the abbreviation for computer-aided design/computer-aided manufacturing.

In the present disclosure, weight percentage (wt. %) values of the various components (e.g., at least a polymerizable component, ceramic fibers and nanoclusters) that make up the composite material are recited. These wt. % values of the composite material are based on a total weight of the composite material and the wt. % values of all the components that are used to form the composite material of the present disclosure always total to a value of 100 wt. %.

The recitation herein of numerical ranges by endpoints is intended to include all numbers subsumed within that range (e.g. 1 to 5 includes 1, 1.5, 2, 2.75, 3, 3.80, 4, and 5).

As used herein, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurement of properties such as contrast ratio and so forth used in the specification and claims can be modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviations found in their respective testing measurements.

As discussed herein, the composite material of the present disclosure includes 4 to 50 weight percent (wt. %) of ceramic fibers, where the wt. % is based on a total weight of the composite material. Ceramic fibers having weight percent's within this range are also possible. For example, the ceramic fibers of the composite material can have weight percent's with a low value of any one of 4, 5, 6, 8, 10, 12, 16 or 18 to a high value of a given range of 50, 48, 45, 42, 40, 38, 36, 34, 32, 30, 28, 24 or 20. Different combinations of the low value and the high value are possible for the wt. % of ceramic fibers. Examples of such combinations include 4 to 40 wt. % of ceramic fibers in the composite material; 8 to 40 wt. % of ceramic fibers in the composite material or 16 to 40 wt. % of ceramic fibers in the composite material, where the wt. % is based on a total weight of the composite material. Any combination of the low value and the high value recited herein can be used to provide a range for the wt. % of ceramic fibers in the composite material.

The ceramic fibers of the composite material also each have a length. As each of the ceramic fibers can have a different length, the lengths of the ceramic fibers can be grouped into percentages of a total number of the ceramic fibers that are either above or below a given length value. For example, the ceramic fiber length "L" is giving by the fraction of the ceramic fibers that are either shorter or longer than a given value. These "L" values include a numerical prefix (e.g., "L10", "L25", "L50", "L75", "L90" or "L99") that indicates the percentage (based on a total number of the ceramic fibers) of the ceramic fibers that have a length that is either less than or equal to a given length value. So, for example, "L10" can denote that 10% of the ceramic fibers are less than or equal to the L10 length value, L50 can denote that 50% of the ceramic fibers are less than or equal to the L50 length value and 50% of the ceramic fibers are greater than the L50 length value (this is also known as the median length) and L90 can denote that 90% of the ceramic fibers are less than or equal to the L90 length value.

For the present disclosure, the length of fifty percent of the ceramic fibers (i.e., the "L50"), based on a total number of the ceramic fibers, is at least 50 micrometers and the length of ninety percent (%) of the ceramic fibers (i.e., the "L90"), based on the total number of the ceramic fibers, is no greater than 500 micrometers. In other words, for the composite material of the present disclosure at least 50% of the ceramic fibers ("L50") have a length that is at least 50 micrometers and at least 90% of the ceramic fibers have a length that is no greater than 500 micrometers. Other values and ranges are possible for the "L" values of the ceramic fibers that either fall below or above a given percentage of the total number of ceramic fibers. For example, the length of sixty-five percent of the ceramic fibers ("L65"), based on a total number of the ceramic fibers, can be at least 100 micrometers and the length of ninety percent of the ceramic fibers ("L90"), based on the total number of the ceramic fibers, can be no greater than 350 micrometers. The L90 values (length of ninety % of the ceramic fibers based on the total number of the ceramic fibers) can also include any one of the following values: less than equal to 475 micrometers; less than equal to 450 micrometers; less than equal to 425 micrometers; less than equal to 400 micrometers; less than equal to 375 micrometers; less than equal to 350 micrometers; less than equal to 325 micrometers; less than equal to 300 micrometers; less than equal to 275 or less than equal to 250 micrometers, while the L50 values (length of fifty % of the ceramic fibers based on a total number of the ceramic fibers) can also include any one of the following values: at least 75 micrometers; at least 100 micrometers; at least 125 micrometers; at least 150 micrometers; at least 175 micrometers; at least 200 micrometers or at least 225 micrometers, where combinations of ranges for the L90 and L50 values are possible. Examples of such ranges for the L90 and L50 values include, but are not limited to, ceramic fibers of the present disclosure having an L90 value of less than equal to 475 micrometers and an L50 value of at least 75 micrometers; an L90 value of less than equal to 475 micrometers and an L50 value of at least 100 micrometers; and an L90 value of less than equal to 475 micrometers and an L50 value of at least 100 micrometers.

The ceramic fibers of the present disclosure can also have an arithmetic mean length. For example, the ceramic fibers of the composite material can an arithmetic mean length of 50 micrometers to less than 500 micrometers. Preferably, the ceramic fibers of the composite material can an arithmetic mean length of 100 micrometers to 170 micrometers. The ceramic fibers can also have an arithmetic mean diameter of 0.5 to 20 micrometers. In one embodiment, the arithmetic mean diameter of the ceramic fibers can be 6 to 15 micrometers. Preferably, the arithmetic mean diameter of the ceramic fibers is 8 to 13 micrometers. Most preferably, the arithmetic mean diameter of the ceramic fibers is 9 to 12 micrometers. It is appreciated that in addition to a circular cross-section for the ceramic fibers, it is also possible to have different cross-sectional shapes. Examples include, but are not limited to, ribbon like, oval (non-circular) and polygonal (e.g., triangular or square), among others known in the art.

The size and shape of the ceramic fibers of the composite material can further be described based on their aspect ratio (e.g., length-to-diameter ratio). It is appreciated that the cross-sectional shape of the ceramic fiber may not be exactly circular. As such, the cross-sectional area of the ceramic fiber can be used to arrive at a "diameter" value to be used for the aspect ratio discussed herein. For the present disclosure an aspect ratio of a median length of the fifty percent of the ceramic fibers that have a length of at least 50 micrometers to a median diameter of the fifty percent of the ceramic fibers that have a length of at least 50 micrometers is at least 5:1 (median length:median diameter).

The ceramic fibers of the present disclosure can have a variety of compositions. Preferably, the ceramic fibers of the present disclosure are at least partially amorphous ceramic fibers. More preferably, the ceramic fibers of the present disclosure are completely amorphous ceramic fibers. The ceramic fibers can be produced in continuous lengths, which are chopped or sheared, as discussed herein, to provide the ceramic fibers of the present disclosure.

The ceramic fibers of the present disclosure can be produced from a variety of commercially available ceramic filaments. Examples of filaments useful in forming the ceramic fibers of the present disclosure include the ceramic oxide fibers sold under the Trademark Nextel™ (3M Company, St. Paul, Minn.). Nextel™ is a continuous filament ceramic oxide fiber having low elongation and shrinkage at operating temperatures, and offer good chemical resistance, low thermal conductivity, thermal shock resistance and low porosity. Specific examples of Nextel™ include Nextel™ 312, Nextel™ 440, Nextel™ 550, Nextel™ 610 and Nextel™ 720. Nextel™ 312 and Nextel™ 440 are refractory aluminoborosilicate that includes $Al_2O_3$, $SiO_2$ and $B_2O_3$. Nextel™ 550 and Nextel™ 720 are aluminosilica and Nextel™ 610 is alumina.

Certain of the Nextel™ ceramic oxide fibers are preferred due to the presence of aluminoborosilicate, which provides for desirable refractive index values and the ability of the composite material to polish to a desired gloss, as presented in the Examples herein. Preferably, the ceramic fibers are formed from Nextel™ 312. Nextel™ 312 has a chemical composition, in weight percent (wt. %), of 62.5 wt. %, $Al_2O_3$, 24.5 wt. % $SiO_2$ and 13 wt. % boron trioxide ($B_2O_3$), where the wt. % are based on the total weight of the ceramic fiber. Nextel™ 312 has a filament diameter of 10 to 12 micrometers, a Refractive Index of 1.568 and a surface area ($m^2/g$), as provided from 3M, of less than 0.2. Nextel™ 440 has a chemical composition of 70 wt. %, $Al_2O_3$, 28 wt. % $SiO_2$ and 2 wt. % $B_2O_3$, a filament diameter of 10 to 12 micrometers, a Refractive Index of 1.614 and a surface area ($m^2/g$), as provided from 3M, of less than 0.2. Nextel™ 550 has a chemical composition of 73 wt. %, $Al_2O_3$ and 27 wt. % $SiO_2$, a filament diameter of 10 to 12 micrometers, a Refractive Index of 1.602 and a surface area ($m^2/g$), as provided from 3M, of less than 0.2.

During manufacture, the NEXTEL™ filaments are coated with organic sizings or finishes which serves as aids in textile processing. Sizing can include the use of starch, oil, wax or other organic ingredients applied to the filament strand to protect and aid handling. Sizings can also include a surface treatment, such as with a silane, where the surface treatment may or may not include polymerizable groups. The sizing can be removed from the ceramic filaments by heat treating the filaments or ceramic fibers as a temperature of 700° C. for one to four hours.

Ceramic fibers according to the present disclosure can also be formed from other suitable ceramic oxide filaments. Examples of such ceramic oxide filaments include those available from Central Glass Fiber Co., Ltd. (e.g., EFH75-01, EFH150-31). Also preferred are aluminoborosilicate glass fibers which are which contain less than about 2% alkali or are substantially free of alkali (i.e., "E-glass" fibers). E-glass fibers are available from numerous commercial suppliers.

As discussed herein, the ceramic fibers of the present disclosure can be cut or chopped so as to provide the percentage of fibers lengths in the ranges discussed herein. Producing ceramic fibers having this range of relatively uniform lengths can be accomplished by cutting continuous filaments of the ceramic material in a mechanical shearing operation or laser cutting operation, among other cutting operations. Given the highly controlled nature of such cutting operations, the size distribution of the ceramic fibers is very narrow, thereby allowing for the length of fifty percent of the ceramic fibers (i.e., the "L50"), based on a total number of the ceramic fibers, to be at least 50 micrometers and the length of ninety percent of the ceramic fibers (i.e., the "L90"), based on the total number of the ceramic fibers, to be no greater than 500 micrometers.

It has been observed that there is a direct correlation between improvements in the handling of the composite material and the narrow size distribution of the ceramic fibers as discussed herein. So, for example, as the size distribution of the ceramic fibers is reduced there is expected to be a significant improvement in the handling of the composite material, all other things being equal. This is a very desirable feature of the present disclosure, especially for dental restorative material applications. In contrast to the ceramic fibers of the present disclosure, milled or ground versions of the ceramic fibers not displaying such a narrow size distribution in the stated ranges produce composite materials that are problematic. For example, if the number of ceramic fibers greater than 500 micrometers is too large their presence in the composite material produces poor handling properties, while if the number of ceramic fibers less than 50 micrometers is too large their presence in the composite material produces less than desirable mechanical properties in the cured composite material.

The ceramic fibers of the present disclosure can also be treated in order to modify their surface properties. For example, treating the ceramic fibers with boiling water can help to removing sizing from the ceramic fibers. Treating the ceramic fibers with boiling water can also help to change the surface area of the ceramic fibers. So, for example, it has been found that etching the surface of boroaluminosilicate fibers (e.g., Nextel™ 312) through a boiling water method helps to leach boron trioxide from these fibers. The boiling water method can include dispersing the ceramic filament or ceramic fibers in deionized water and boiling the mixture for a predetermined time at atmospheric pressure. Predetermined times for boiling can depend upon the composition of any sizing used with the ceramic fiber and/or the composition of the ceramic fiber itself. Examples of suitable times for the predetermined times for the boiling water method include, but are not limited to, 10 minutes (min.), 15 min., 20 min., 25 min., 30 min., 35 min., 40 min., 45 min., 50 min., 55 min., 60 min., 65 min., 70 min., 75 min., 80 min., 85 min., 90 min., 95 min., 100 min., 105 min., 110 min., 115 min. and 120 min. Other predetermined times are possible. In one embodiment, the Nextel™ 312 filament having undergone the boiling water method for 90 min. had less than 14 weight percent of boron trioxide based on the total weight of the ceramic fibers.

Sizing and/or specific portions of the ceramic fiber could also be removed through etching with an acid or a base. A heat treatment can also be used to remove sizing from the ceramic fiber. It is also possible to remove any sizing and/or specific portions of the ceramic fiber through laser or plasma ablation.

In addition to removing components from the ceramic fibers, treating the ceramic fibers to modify their surface properties also causes an increase in the surface area of the ceramic fibers. For example, ceramic fibers of the present disclosure can be treated (e.g., with boiling water for 90 min.) so as to increase their surface area to at least 10 square meters per gram ($m^2/g$). Measurements of the surface area of the ceramic fibers as discussed herein can be accomplished using the technique developed by Brunauer, Emmett and Teller, see S. Brunauer, "Physical Adsorption" (Princeton University Press, Princeton, N.J., 1945), commonly referred to as "BET" gas adsorption.

The result is an increase in the surface area of these ceramic fibers and subsequently better coupling of these ceramic fibers into the polymerizable component. Using such ceramic fibers helps the composite material of the present disclosure to retain good mechanical properties such as flexural strength, which is an important property for dental restorative materials, as well as for good composite performance in general applications. One or more (e.g., two or more) of a coupling agent can also be used with the ceramic fiber after they have been treated to remove any sizing and/or to increase their surface area. One or more of the coupling agent can also be used with the filler particles, as discussed herein. So, combinations of two or more coupling agents, as discussed herein, can be used with the ceramic fiber and filler particles, when present, in the composite material. In some embodiments, such coupling agents can help to provide a chemical bond (e.g., a covalent bond) between the polymerizable component and the ceramic fibers and, when present, the filler particles. The coupling agent is a compound capable of reacting with both the polymerizable component and the ceramic fibers and the filler particles (when present), thereby acting as interface between the polymerized polymerizable component and the ceramic fibers and the filler particles (when present). The ceramic fibers and the filler particles (when present) can be treated with the coupling agent prior to admixing with the polymerizable component. Thus, in some embodiment, the coupling agent includes a polymerizable group, such as for example one or more epoxy, acrylate and/or (meth)acrylate groups. In other embodiments, the coupling agent does not include polymerizable group.

For the various embodiments, the coupling agent can be selected from the group consisting of an organosilane coupling agent, a titanate coupling agent, a zirconate coupling agent, an acidic coupling agent or a combination thereof. The coupling agent may be applied to the inorganic materials (e.g., the ceramic fibers and filler particles, when present) as a pre-treatment and/or added to the polymerizable component.

Organosilane coupling agents have the general formula $R_nSiX_{(4-n)}$. The functional group "X" is involved in the reaction with the substrate, where X is independently at each occurrence a hydrolyzable group such as an alkoxy, an acyloxy or an amine. R is a non-hydrolyzable organic radical that possesses a functionality that enables the organosilane coupling agent to bond with, or improve compatibility with, organic polymers and the like. Suitable examples of organosilane coupling agents include gamma-methacryloxypropyltrimethoxysilane, gamma-methacryloxyoctyltrimethoxysilane, gamma-mercaptopropyltriethoxysilane, gamma-aminopropyltrimethoxysilane, beta-(3,4-epoxycyclohexyl)ethyltrimethoxysilane, gamma-glycidoxypropyltrimethoxysilane, and the like. Other suitable examples of organosilane coupling agents include n-octyltrimethoxysilane, phenyltrimethoxysilane, and the like. Mixtures of organosilane coupling agents may be used.

Titanate coupling agents include a family of monoalkoxy titanates useful in conjunction with the ceramic fibers and the filler particles, when present. Titanate couplers typically have three pendant organic functional groups. The titanate couplers also act as plasticizers to enable much higher loadings and/or to achieve better flow. A suitable example of a titanate coupling reagent includes methoxydiethyleneglycol trimethacryloyl titanate.

Zirconate coupling agents include 2,2-di(allyloxymethyl) butyl trimethacryloyl zirconate.

Acidic coupling agents include mono-2-(methacryloyloxy)ethyl succinate.

The composite material of the present disclosure is hardenable due the presence of the polymerizable component. The composite material includes 20 to 40 wt. % of the polymerizable component. In some embodiments, the composite material can be hardened (e.g., polymerized by conventional photopolymerization and/or chemical polymerization techniques) prior to applying it to an oral surface. In other embodiments, the composite material can be hardened (e.g., polymerized by conventional photopolymerization and/or chemical polymerization techniques) after it has been applied to an oral surface.

Examples of the polymerizable component include, but are not limited to, those having sufficient strength, hydrolytic stability, and non-toxicity to render them suitable for use in the oral environment. Examples of such materials include acrylates, methacrylates, urethanes, carbamoylisocyanurates and epoxy resins (e.g., those shown in U.S. Pat. No. 3,066,112 (Bowen); U.S. Pat. No. 3,539,533 (Lee II et al.); U.S. Pat. No. 3,629,187 (Waller); U.S. Pat. No. 3,709,866 (Waller); U.S. Pat. No. 3,751,399 (Lee et al.); U.S. Pat. No. 3,766,132 (Lee et al.); U.S. Pat. No. 3,860,556 (Taylor); U.S. Pat. No. 4,002,669 (Gross et al.); U.S. Pat. No. 4,115,346 (Gross et al.); U.S. Pat. No. 4,259,117 (Yamauchi et al.); U.S. Pat. No. 4,292,029 (Craig et al.); U.S. Pat. No. 4,308,190 (Walkowiak et al.); U.S. Pat. No. 4,327,014 (Kawahara et al.); U.S. Pat. No. 4,379,695 (Orlowski et al.); U.S. Pat. No. 4,387,240 (Berg); U.S. Pat. No. 4,404,150 (Tsunekawa et al.)); and mixtures and derivatives thereof.

In certain embodiments, the polymerizable component of the composite material is photopolymerizable, i.e., the polymerizable component contains a photoinitiator system that upon irradiation with actinic radiation initiates the polymerization (or hardening) of the composite material. In other embodiments, the polymerizable component of the composite material is chemically hardenable, i.e., the polymerizable component contains a chemical initiator (i.e., initiator system) that can polymerize, cure, or otherwise harden the composite material without dependence on irradiation with actinic radiation. Such chemically hardenable compositions are sometimes referred to as "self-cure" compositions.

The polymerizable component typically includes one or more ethylenically unsaturated compounds with or without acid functionality. Examples of useful ethylenically unsaturated compounds include acrylic acid esters, methacrylic acid esters, hydroxy-functional acrylic acid esters, hydroxy-functional methacrylic acid esters, and combinations thereof.

The composite material, especially in photopolymerizable implementations, may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth) acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth) acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired. In some embodiments, a methacryloyl-containing compound may be utilized.

The polymerizable component may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments, the polymerizable component includes a compound selected from the group consisting of dimethacrylates of polyethylene glycols of 200 to 1000 weight average molecular weight, such as PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), 2 to 10 mole ethoxylated Bisphenol-A dimethacrylate (Bis-EMA), such as bisEMA6 as described in U.S. Pat. No. 6,030,606 (Holmes), NPGDMA (neopentylglycol dimethacrylate), glycerol dimethacrylate, 1,3-propanediol dimethacrylate and 2-hydroxethyl methacrylate. Various combinations of these hardenable components can be used. For certain embodiments, including any one of the above embodiments, the polymerizable resin comprises a compound selected from the group consisting of 2,2-bis[4-(2-hydroxy-3-methacryloyloxypropoxy)phenyl]propane (bisGMA), triethyleneglycol dimethacrylate (TEGDMA), urethane dimethacrylate (UDMA), 2 to 10 mole ethoxylated Bisphenol-A dimethacrylate (bisEMA), dimethacrylates of polyethylene glycols of 200 to 1000 weight average molecular weight, glycerol dimethacrylate, 1,3-propanediol dimethacrylate, and a combination thereof.

When the composite material contains an ethylenically unsaturated compound without acid functionality, it is generally present in an amount of at least 5% by weight, more typically at least 10% by weight, and most typically at least 15% by weight ethylenically unsaturated compounds without acid functionality, based on the total weight of the unfilled composition. The compositions of the present disclosure typically include at most 95% by weight, more typically at most 90% by weight, and most typically at most 80% by weight ethylenically unsaturated compounds without acid functionality, based on the total weight of the unfilled composition.

In some embodiments, the polymerizable component may include one or more ethylenically unsaturated compounds with acid functionality. As used herein, ethylenically unsaturated compounds "with acid functionality" is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α, β-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable component system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain preferred compositions of the present disclosure include an ethylenically unsaturated compound with acid functionality having at least one P—OH moiety.

When the composition contains an ethylenically unsaturated compound with acid functionality, it is generally present in an amount of at least 1% by weight, more typically at least 3% by weight, and most typically at least 5% by weight ethylenically unsaturated compounds with acid functionality, based on the total weight of the unfilled composition. The compositions of the present disclosure typically include at most 80% by weight, more typically at most 70% by weight, and most typically at most 60% by weight ethylenically unsaturated compounds with acid functionality, based on the total weight of the unfilled composition.

For free radical polymerization (hardening), an initiation system can be selected from systems which initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

In certain embodiments, one or more thermally activated initiators are used to enable thermal hardening of the polymerizable component. Examples of thermal initiators include peroxides and azo compounds such as benzoyl peroxide, lauryl peroxide, 2,2-azobis-isobutyronitrile (AIBN).

In certain embodiments, the thermally activated initiator is chosen such that appreciable amounts of free-radical initiating species are not produced at temperatures below about 100° C. "Appreciable amounts" refers an amount sufficient to cause polymerization and/or crosslinking to the extent that a noticeable change in properties (e.g., viscosity, moldability, hardness, etc.) of the composite material occurs. For certain embodiments, the initiator is activated within the temperature range of 120 to 140° C., or, in some embodiments, 130 to 135° C. For certain of these embodiments, the initiator is an organic peroxide which can be thermally activated to produce appreciable amounts of free-radical initiating species within any of these temperature ranges. For certain of these embodiments, the initiator is selected from the group consisting of dicumyl peroxide, t-butyl peroxide, and a combination thereof. For certain of these embodiments, the initiator is dicumyl peroxide. In other embodiments, the initiator is selected from 2,5-bis(tert-butylperoxy)-2,5-dimethylhexane; 2,5-bis(tert-butylperoxy)-2,5-dimethyl-3-hexyne; bis(1-(tert-butylperoxy)-1-methylethy)benzene; tert-butyl peracetate; tert-butyl peroxybenzoate; cumene hydroperoxide; 2,4-pentanedione peroxide; peracetic acid, and combinations thereof.

For certain embodiments, the thermally activated initiator is present in the composition in an amount of at least 0.2 percent based upon the weight of the polymerizable component. For certain of these embodiments, the initiator is present in an amount of at least 0.5 percent. For certain of these embodiments, the initiator is present in the composition in the amount of not more than 3 percent based upon the weight of the polymerizable component. For certain of these embodiments, the initiator is present in an amount of not more than 2 percent.

In certain embodiments, the composition may additionally be photopolymerizable, i.e., the composition contains a photoinitiator system that upon irradiation with actinic radiation initiates polymerization (curing or hardening) of the composition. Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Suitable iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Suitable photosensitizers are monoketones and diketones that absorb some light within a range of 400 nm to 520 nm (preferably, 450 nm to 500 nm). Particularly suitable compounds include alpha diketones that have light absorption within a range of 400 nm to 520 nm (even more preferably, 450 to 500 nm). Suitable compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other useful photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application 0 173 567 A2 (Ying).

Commercially available phosphine oxide photoinitiators capable of free-radical initiation when irradiated at wavelength ranges of different from 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

The phosphine oxide initiator may be used in the photopolymerizable composition in catalytically effective amounts, such as from 0.1 weight percent to 5.0 weight percent, based on the total weight of the unfilled composition.

Tertiary amine reducing agents may be used in combination with an acylphosphine oxide. Illustrative tertiary amines useful in the disclosure include ethyl 4-(N,N-dimethylamino)benzoate and N,N-dimethylaminoethyl methacrylate. When present, the amine reducing agent is present in the photopolymerizable composition in an amount from 0.1 weight percent to 5.0 weight percent, based on the total weight of the unfilled composition. Useful amounts of other initiators are well known to those of skill in the art.

Polymerizable components made from cationically curable material suitable for use in the present disclosure can also include epoxy resins. Epoxy resins impart high toughness to composites, a desirable feature, for example, dental mill blanks. Epoxy resins may optionally be blended with various combinations of polyols, methacrylates, acrylates, or vinyl ethers. Preferred epoxy resins include diglycidyl ether of bisphenol A (e.g. EPON 828, EPON 825; Shell Chemical Co.), 3,4-epoxycyclohexylmethyl-3-4-epoxy cyclohexene carboxylate (e.g. UVR-6105, Union Carbide), bisphenol F epoxides (e.g. GY-281; Ciba-Geigy), and polytetrahydrofuran.

As used herein, "cationically active functional groups" is a chemical moiety that is activated in the presence of an initiator capable of initiating cationic polymerization such that it is available for reaction with other compounds bearing cationically active functional groups. Materials having cationically active functional groups include cationically polymerizable epoxy resins. Such materials are organic compounds having an oxirane ring, i.e., a group which is polymerizable by ring opening. These materials include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The weight average molecular weight of the epoxy-containing materials may vary from about 58 to about 100,000 or more. Molecular weights (e.g., weight average molecular weights) for the present disclosure are measured using size exclusion chromatography with polystyrene standards.

Useful epoxy-containing materials include those which contain cyclohexane oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, which is incorporated herein by reference.

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar. Other types of useful materials having cationically active functional groups include vinyl ethers, oxetanes, spiro-orthocarbonates, spiro-orthoesters, and the like.

For hardening polymerizable components comprising cationically active functional groups, an initiation system can be selected from systems which initiate polymerization via radiation, heat, or redox/auto-cure chemical reaction. For example, epoxy polymerization may be accomplished by the use of thermal curing agents, such as anhydrides or amines. A particularly useful example of an anhydride curing agent would be cis-1,2-cyclohexanedicarboxylic anhydride.

Alternatively, initiation systems for polymerizable components comprising cationically active functional groups are those that are photoactivated. The broad class of cationic photoactive groups recognized in the catalyst and photoinitiator industries may be used in the practice of the present disclosure. Photoactive cationic nuclei, photoactive cationic moieties, and photoactive cationic organic compounds are art recognized classes of materials as exemplified by U.S. Pat. Nos. 4,250,311; 3,708,296; 4,069,055; 4,216,288; 5,084,586; 5,124,417; 4,985,340, 5,089,536, and 5,856,373, each of which is incorporated herein by reference.

The cationically-curable materials can be combined with a three component or ternary photoinitiator system, as described above. Three component initiator systems are also described in U.S. Pat. No. 6,025,406 and U.S. Pat. No. 5,998,549, each of which is incorporated herein by reference.

The chemically hardenable compositions may include redox cure systems that include a polymerizable component (e.g., an ethylenically unsaturated polymerizable component) and redox agents that include an oxidizing agent and a reducing agent.

The reducing and oxidizing agents should react with or otherwise cooperate with one another to produce free-radicals capable of initiating polymerization of the polymerizable component (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions.

Useful reducing agents include ascorbic acid, ascorbic acid derivatives, and metal complexed ascorbic acid compounds; amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure.

The reducing and oxidizing agents are present in amounts sufficient to permit an adequate free-radical reaction rate. This can be evaluated by combining all of the ingredients of the composition except for the optional filler, and observing whether or not a hardened mass is obtained.

Typically, the reducing agent, if used at all, is present in an amount of at least 0.01% by weight, and more typically at least 0.1% by weight, based on the total weight (including water) of the components of the composition. Typically, the reducing agent is present in an amount of no greater than 10% by weight, and more typically no greater than 5% by weight, based on the total weight (including water) of the components of the composition.

Typically, the oxidizing agent, if used at all, is present in an amount of at least 0.01% by weight, and more typically at least 0.10% by weight, based on the total weight (including water) of the components of the composition. Typically, the oxidizing agent is present in an amount of no greater than 10% by weight, and more typically no greater than 5% by weight, based on the total weight (including water) of the components of the composition.

When used as a dental restorative material, the composite material can have a variety of weight percent values for the ceramic fibers and/or the nanoclusters depending upon the dental application. So, for example, if used as a sealant, the composite material of the disclosure can be filled with the ceramic fibers and/or the nanoclusters so as to provide a flowable composite. In such implementations, the viscosity of the composite material is sufficiently low to allow its penetration into pits and fissures of occlusal tooth surfaces as well as into etched areas of enamel, thereby aiding in the retention of the composite material. In applications where high strength or durability are desired (e.g., anterior or posterior restoratives, prostheses, crown and bridge cements, artificial crowns, artificial teeth and dentures) the loading level of the ceramic fibers and the nanoclusters can be tailored so as to provide a more rigid composite.

The composite material further includes 20 to 70 wt. % of nanoclusters. The composite material can also include other value ranges for the nanoclusters. For example, the composite material can also include for the wt. % of the nanoclusters lower limit values of: 20, 22, 25, 30, 35 or 40, and upper limit values of 70, 65, 64, 60, 55, 50 or 45. This allows for a variety of possible ranges for the wt. % of the nanoclusters in the composite material. Examples of such ranges include, but are not limited to, 25 to 70 wt. % of nanoclusters, 25 to 65 wt. % of nanoclusters, 25 to 60 wt. % of nanoclusters, 25 to 55 wt. % of nanoclusters, where a range of 22 to 64 wt. % of nanoclusters is preferred.

As discussed herein, for a given combination of components that forms the composite material the wt. % of each of the components adds to 100 wt. % (wt. % based on the total weight of the composite material). Preferably, the nanoclusters are silica-zirconia nanoclusters formed from silica nanoparticles and zirconia that associate by relatively weak intermolecular forces that cause the silica nanoparticles and zirconia to clump together, even when dispersed in the polymerizable component of the present disclosure. The silica nanoparticles and zirconia (the "primary particles" that form the silica-zirconia nanoclusters) can have a mean diameter of 1 nanometer (nm) to 200 nm, where the resulting silica-zirconia nanoclusters can have a longest dimension in the micrometer range (e.g., 10 micrometers) from the association or "nanocluster" of the silica nanoparticles and zirconia. The primary particles forming the silica-zirconia nanoclusters (e.g., the silica nanoparticles and zirconia) can be grouped together in an amorphous cluster formation. The cluster formation of the silica nanoparticles and zirconia, however, is not limited to such an amorphous cluster formation.

Silica-zirconia nanoclusters may be prepared by mixing a nanosilica sol together with a preformed nanozirconia particulate sol or a zirconium salt (e.g., an acetate or nitrate salt) solution. When a nanozirconia sol is used it is typically composed of crystalline zirconia nanoparticles. The nanosilica sol typically comprises silica particles having a mean diameter from 1 to 200 nm, more typically 10 nm to 100 nm, even more typically from 15 nm to 60 nm, most typically from 15 nm to 35 nm, with a mean particle diameter of about 20 nm being particularly well-suited for fabrication of the silica-zirconia nanoclusters.

The zirconia sol typically comprises zirconia particles that are small enough to not scatter the majority of visible light, but are large enough to refract shorter wavelength blue light to give the opalescent effect. A zirconia sol having a mean particle size from about 3 nm to about 30 nm is suitable for forming the silica-zirconia nanoclusters. Typically, the zirconia particles in the sol have a mean particle diameter from 5 nm to 15 nm, more typically from 6 nm to 12 nm, and most typically from 7 nm to 10 nm. When mixed together under acidic conditions where the sol mixture is stable, such as at a pH of below 2, the preformed zirconia nanoparticles form a structure with the silica nanoparticles on gelling and drying that gives the desired opalescence character while maintaining a high level of optical translucency of the final composite material.

NALCO 1042 silica sol (Ecolab, Inc., St. Paul, Minn.), NALCO 1034A, or other commercially available colloidal silica sols may be used. If a base-stabilized sol is used, typically it will first be subjected to ion exchange in order to remove sodium, for example, with an AMBERLITE IR-120 ion exchange resin, or pH adjusted with nitric acid. It is usually desirable to pH adjust the silica to below 1.2, typically about 0.8 to about 1.0, and then add the zirconia to it slowly, to prevent localized gelation and agglomeration. The pH of the resultant mixture is typically about 1.1 to about 1.2. Suitable colloidal silica sols are available from a variety of vendors, including Nalco (Ecolab), H.C. Stark, Nissan Chemical (Snowtex), Nyacol, and Ludox (DuPont). The selected sol should have silica particles that are discrete and of the appropriate size specified herein. The silica sol may be treated to provide a highly acidic silica sol (e.g., nitrate stabilized) that can be mixed with the zirconia sol without gelation.

The zirconia sol may be obtained using a process described, for example, in U.S. Pat. No. 6,376,590 (Kolb, et al.), or U.S. Pat. No. 7,429,422 (Davidson et al.) the disclosures of which are incorporated by reference herein. As used herein, the term "zirconia" refers to various stoichiometries for zirconium oxides, most typically $ZrO_2$, and may also be known as zirconium oxide or zirconium dioxide. The zirconia may contain up to 30 weight percent of other chemical moieties such as, for example, $Y_2O_3$ and organic material.

The silica-zirconia nanoclusters can be prepared by mixing together the nanosilica sol with the nanozirconia sol, and heating the mixture to at least 450° C. Typically, the mixture is heated for 4 to 24 hours at a temperature between about 400 to about 1000° C., more typically from about 450 to about 950° C., to remove water, organic materials, and other volatile components, as well as to potentially weakly aggregate the particles (not required). Alternatively, or in addition, the sol mixture may undergo a different processing step to remove water and volatiles. The resulting material may be milled or ground and classified to remove large aggregates.

The silica-zirconia nanoclusters may then be surface treated with, for example, a silane prior to mixing with a polymerizable component.

The composite material of the present disclosure can also include, optionally, one or more of filler particles in addition to the ceramic fibers. Such filler particles may be selected from one or more of a wide variety of materials suitable for incorporation in composite materials used for dental applications, such as filler particles currently used in dental restorative compositions, and the like. The choice of the filler particle can affect properties of the composite material such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. In this way, the appearance of the composite material can, if desired, be made to closely approximate the appearance of natural dentition.

Filler particles may be selected from one or more of material suitable for incorporation in compositions used for medical applications, such as filler particles currently used in dental restorative compositions and the like. The maximum particle size (the largest dimension of a particle, generally, the diameter) of the filler particles is typically less than 20 micrometers, more typically less than 10 micrometers, and most typically less than 5 micrometers. The number average particle size diameter of the filler particles is typically no greater than 100 nm, and more typically no greater than 75 nm. The filler particles can have a unimodal or polymodal (e.g., bimodal) particle size distribution. The filler particles can be an inorganic material. It can also be a crosslinked organic material that is insoluble in the polymerizable component, and is optionally filled with inorganic filler. The filler particle should in any event be suitable for use in the mouth. The filler particle can be radiopaque, radiolucent or non-radiopaque. The filler particle typically is substantially insoluble in water. The filler particle may have a variety of shapes, including but not limited to equiaxed, spherical, polyhedral, oblong, lenticular, toroidal or whisker.

Examples of suitable filler particles are naturally-occurring or synthetic materials such as quartz, nitrides (e.g., silicon nitride); glasses containing, for example Ce, Sb, Sn, Sr, Ba, An, and Al; colloidal silica; feldspar; borosilicate glass; kaolin; talc; titania; and zinc glass; low Mohs hardness fillers such as those described in U.S. Pat. No. 4,695,251; and submicrometer silica particles (e.g., pyrogenic silicas such as the "Aerosil" Series "OX 50", "130", "150" and "200" silicas sold by Degussa Akron, Ohio and "Cab-O-Sil M5" silica sold by Cabot Corp. Tuscola, Ill.) and non-vitreous microparticles of the type described in U.S. Pat. No. 4,503,169. Silane-treated zirconia-silica (Zr—Si) filler particles are especially useful in certain embodiments.

Metallic filler particles may also be incorporated, such as metal filler particles made from a pure metal such as those of Groups 4, 5, 6, 7, 8, 11, or 12, aluminum, indium, and thallium of Group 13, and tin and lead of Group 14, or alloys thereof, where the elements from the recited Groups are found in the 8 Jan. 2016 version of the IUPAC Periodic Table. Conventional dental amalgam alloy powders, typically mixtures of silver, tin, copper, and zinc, may also optionally be incorporated. The metallic filler particles preferably have a number average particle size diameter of about 1 micrometer to about 100 micrometers, more preferably 1 micrometer to about 50 micrometers. Mixtures of these filler particles are also contemplated, as well as combination filler particles made from organic and inorganic materials.

Preferably, the composite material can include, when present, up to 12 wt. % of nanoparticles as the filler particles based on the total weight of the composite material. For example, the composite material can include 2 to 12 wt. % of nanoparticles as the filler particles based on the total weight of the composite material. As defined herein, the nanoparticles are discrete non-fumed metal oxide nanoparticles. As discussed herein, for a given combination of components that forms the composite material the wt. % of each of the components adds to 100 wt. % (wt. % based on the total weight of the composite material). Examples of discrete non-fumed metal oxide nanoparticles include discrete non-fumed heavy metal oxide nanoparticles. In addition, the discrete non-fumed metal oxide nanoparticles can include both discrete non-fumed heavy metal oxide nanoparticles and discrete non-fumed non-heavy metal oxide nanoparticles. Examples of discrete non-fumed non-heavy metal oxide nanoparticles include nanosilica, while examples of discrete non-fumed heavy metal oxide nanoparticles include zirconia, yttria and lanthana particles. Discrete non-fumed heavy metal oxide nanoparticles may be prepared from heavy metal oxide sols as described according to U.S. Pat. No. 6,736,590 (Kolb et al.) or U.S. Pat. No. 7,429,422 (Davidson et al.). Discrete non-fumed non-heavy metal oxides may be purchased as colloidal silica. The discrete non-fumed nanoparticles of silica may be prepared from dispersions, sols, or solutions of at least one precursor. Processes of this nature are described, for example, in U.S. Pat. No. 4,503,169 (Randklev) and GB Patent No. 2291053 B. The discrete non-fumed metal oxide nanoparticles may also be surface treated with, for example, a silane prior to mixing with a polymerizable component.

The discrete non-fumed metal oxide nanoparticles are typically finely divided with a unimodal or polymodal (e.g., bimodal) particle size distribution. The maximum particle size (the largest dimension of a particle, generally, the diameter) of the discrete non-fumed metal oxide nanoparticles is typically 5 nm to 200 nm, more typically 5 nm to 100 nm, and most typically 5 nm to 80 nm.

Other suitable filler particles are disclosed in U.S. Pat. No. 6,387,981 (Zhang et al.); U.S. Pat. No. 6,572,693 (Wu et al.); U.S. Pat. No. 6,730,156 (Windisch); and U.S. Pat. No. 6,899,948 (Zhang); U.S. Pat. No. 7,022,173 (Cummings et al); U.S. Pat. No. 6,306,926 (Bretscher et al); U.S. Pat. No. 7,030,049 (Rusin et al); U.S. Pat. No. 7,160,528 (Rusin); U.S. Pat. No. 7,393,882 (Wu et al); U.S. Pat. No. 6,730,156 (Windisch et al); U.S. Pat. No. 6,387,981 (Zhang et al); U.S. Pat. No. 7,090,722 (Budd et al); U.S. Pat. No. 7,156,911 (Kangas et al); U.S. Pat. No. 7,361,216 (Kolb et al); as well as in International Publication No. WO 03/063804 (Wu et al.), incorporated herein by reference. Filler particles described in these references include nanosized silica particles, nanosized metal oxide particles, and combinations thereof. Nanofillers are also described in U.S. Pat. No. 7,085,063 (Kangas et al.); U.S. Pat. No. 7,090,721 (Craig et al.) and U.S. Pat. No. 7,649,029 (Kolb et al.); and U.S. Patent Publication Nos. 2010/0089286 (Craig et al); US 2011/0196062 (Craig et al), all incorporated herein by reference. As discussed herein, the surface of the filler particles may, optionally, be treated with a surface treatment, as discussed herein, in order to enhance the bond between the filler and the polymerizable component. In addition, the ceramic fibers and filler particles, when filler particles are present, may be modified with more than one (e.g., two or more) of the surface treatments discussed herein (e.g., coupling agents and/or surface treatments). For example, the same surface treatments may be used for each of the ceramic fibers, while different surface treatments may be used for the filler particles, when present. Different surface treatments may also be used for two or more groups of the ceramic fibers and filler particles, when present in the composite material. For example, the ceramic fibers to be used in the composite material can include a first group of the ceramic fibers that have a surface treatment that is compositionally different than a second group of the ceramic fibers used in the composite material.

As discussed herein, to achieve good aesthetics in a composite material, the optical properties of the components of the composite need to be highly matched. Examples of such optical properties for the components include not only the shade and the color of the components, but also how well the refractive index of the fillers (e.g., the ceramic fibers) match the refractive index of the hardened polymerizable component. Matching the refractive index of the components helps to minimize the scattering of light as it passes through the material, thereby helping to provide a more translucent material. So, for example, the ceramic fibers of the present disclosure preferably have a refractive index value within 0.1 or less of the refractive index of the hardened polymerizable component. More preferable is where the ceramic fibers of the present disclosure preferably have a refractive index value within 0.05 or less of the refractive index of the hardened polymerizable component. Most preferable is where the ceramic fibers of the present disclosure preferably have a refractive index value within 0.005 or less of the refractive index of the hardened polymerizable component.

Examples of refractive index values for the ceramic fibers include ceramic fibers have a refractive index value of 1.40 to 1.65. Preferably, the refractive index value of the ceramic fibers is 1.50 to 1.58. Most preferably, the refractive index value of the ceramic fibers is 1.52 to 1.56. A preferred method for adjusting the refractive index of the ceramic fibers is by altering the ratio of oxide of silicon to ceramic metal oxide. The ceramic fibers refractive index can be approximately predicted by interpolation based on a comparison of the relative volume percent of silica to ceramic metal oxide in the starting mixtures. When additional filler(s) are used with the ceramic fibers their refractive index values can also be matched within the ranges provided herein.

The composite material of the present disclosure can be prepared by combining all the various components using conventional mixing techniques. The resulting composite material may optionally contain additional fillers (in addition to the ceramic fibers and nanoclusters), solvents, water, and/or other additives as described herein. Typically, photopolymerizable composite materials of the disclosure are prepared by admixing, under "safe light" conditions, the components of the composite material. Suitable inert solvents may be employed if desired when affecting this mixture. A solvent may be used which does not react appreciably with the components of the composite material.

Examples of suitable solvents include alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), or mixtures thereof. If desired, the composite material of the disclosure may contain additives such as indicators, dyes (including photobleachable dyes), pigments, inhibitors, accelerators, viscosity modifiers, wetting agents, antioxidants, tartaric acid, chelating agents, buffering agents, stabilizers, diluents, and other similar ingredients that will be apparent to those skilled in the art. Surfactants, for example, nonionic surfactants, cationic surfactants, anionic surfactants, and combinations thereof, may optionally be used in the compositions. Useful surfactants include non-polymerizable and polymerizable surfactants.

Additionally, medicaments or other therapeutic substances can be optionally added to the composite material. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental restorative materials. Combination of any of the above additives may also be employed. The selection and amount of any one such additive can be selected by one of skill in the art to accomplish the desired result without undue experimentation.

The amounts and types of each ingredient in the composite material can be adjusted to provide the desired physical and handling properties before and after polymerization. For example, the polymerization rate, polymerization stability, fluidity, compressive strength, tensile strength and durability of the dental restorative material typically may be adjusted, in part, by altering the types and amounts of polymerization initiator(s) and the loading and particle size distribution of filler(s). Such adjustments typically are carried out empirically based on previous experience with composite materials. When the composite material is used in a dental application, any tooth surface receiving the composite material can optionally be pre-treated with a primer and/or an adhesive by methods known to those skilled in the art.

The composite material can be supplied in a variety of forms including one-part systems and multi-part systems, e.g., two-part paste/paste systems. Other forms employing multi-part combinations (i.e., combinations of two or more parts), each of which is in the form of a powder, liquid, gel, or paste are also possible. The various components of the composite material may be divided up into separate parts in whatever manner is desired; however, in a redox multi-part system, one part typically contains the oxidizing agent and another part typically contains the reducing agent, though it is possible to combine the reducing agent and oxidizing agent in the same part of the system if the components are kept separated, for example, through use of microencapsulation.

The components of the composite material can be included in a kit, where the contents of the composite material are packaged in at least one container to hold the composite material and allow for storage of the components until they are needed. More than one of the composite materials discussed herein can be included in the kit. In addition to the composite material(s) of the present disclosure, the kit can also include at least one dental component selected from the group of a cement, an adhesive, an abrasive, a polishing paste, an instrument, software, a mill, a CAD/CAM system, a composite, a porcelain, a stain, a bur, an impression material, a dental mill blank or a combination thereof.

The components of the composite material can be mixed and clinically applied using conventional techniques. A curing light is generally required for the initiation of photopolymerizable composite materials. The composite material may be in the form of composites or restoratives that adhere very well to dentin and/or enamel. Optionally, a primer layer can be used on the tooth tissue on which the composite material is used.

The composite material of the present disclosure can be hardended to make a dental product. Hardening the composite material can be accomplished based on the type of dental product being produced. For example, the composite material can be hardened, when appropriate, using heat, light, microwave, e-beam, fusing or chemical cure. Once hardened, the dental product and/or dental mill blank of the present disclosure can be trimmed if necessary; and optionally, mounted on a holder stub or post if necessary. The dental product can be selected from the group consisting of a dental restorative (e.g., a sealant, an inlay, an onlay or a bridge), a dental adhesive, a dental mill blank, a dental cement, a dental prostheses, an orthodontic device, an orthodontic adhesive, a dental casting material, artificial crowns, anterior fillings, posterior fillings, and cavity liners or a dental coating.

The dental mill blank of the present disclosure is a block (three dimensional article) of material from which a dental article can be machined. A dental mill blank may have a size suitable for the machining of one or more dental articles. The dental mill blank of the present disclosure can also include a mounting post or frame to facilitate affixation of the blank in a milling machine for milling a dental restorative. A mounting post or frame functions as handle by which a blank is held as it undergoes the milling process. An example of a device for such milling processes can include a CAM machine controlled by data provided by a CAD system (e.g., a CNC machine) for the shape of the desired dental article. These machines produce dental prostheses by cutting, milling, and grinding the near-exact shape and morphology of a required restorative with greater speed and lower labor requirements than conventional hand-made procedures. By using a CAD/CAM milling device, the prosthesis can be fabricated efficiently and with precision. Other machining process can include abrading, polishing, controlled vaporization, electronic discharge milling (EDM), cutting by water jet or laser or other method of cutting, removing, shaping or milling material. After milling, some degree of finishing, polishing and adjustment may be necessary to obtain a custom fit into the mouth and/or aesthetic appearance.

The composite material of the present disclosure can also be used near or on a tooth surface. For example, the composite material can be placed near or on a tooth surface, where the shape or topography of the composite material near or on the tooth surface can be changed prior to hardening the composite material. Changing the shape of the composite material near or on the tooth surface can include shaping the composite material into a dental product selected from the group consisting of a dental prostheses, an orthodontic device, a dental crown, an anterior filling, a posterior filing or a cavity liner. These steps can be followed sequentially or in a different order. For example, in a preferred embodiment where the dental restorative material is a dental mill blank or a prosthesis, the hardening step is generally completed prior to changing the topography of the material. Changing the topography of the material can be accomplished in various ways, including manual manipulation using hand held instruments, or by machine or computer aided apparatus, such as a CAD/CAM milling machine in the case of prostheses and dental mill blanks. Optionally, a finishing step can be performed to polish, finish, or apply a coating on the dental restorative material.

The features and advantages of this disclosure are further illustrated by the following examples, which are in no way intended to be limiting thereof. The particular materials and amounts thereof recited in these examples, as well as other conditions and details, should not be construed to unduly limit this disclosure. Unless otherwise indicated, all parts and percentages are on a weight basis, all water is deionized water, and all molecular weights are weight average molecular weight.

EXAMPLES

Unless otherwise indicated, the methods discussed herein were performed at room temperature (23° C.) and at atmospheric pressure. All commercial materials were used as obtained from the vendor. Unless otherwise specified, all materials are from Sigma-Aldrich Corp. (St. Louis, Mo.).

The testing methods use the following abbreviations: kg, kilogram; s, second(s); cm, centimeter; mm, millimeter; in., inch; min, minute(s); hr, hour; ° C., degree Celsius; %, percent; kN, kilonewton; MPa, megapascals; GPa, gigapascals; nm, nanometer; mW, milliwatt; rpm, rotations per minute; gf, gram-force; and RI, refractive index; psi, pounds per square inch gauge; ml, milliliter; g, grams; μm, micrometer; SEM, Scanning Electron Microscopy; LED, light emitting diode.

Testing Methods

Sixty Degree Gloss

A sixty degree gloss was measured using a Novo-Curve (Rhopoint Instrument, St. Leonards-on-Sea, East Sussex, UK) per ASTM D2457.

Length Measurement—Optical Microscope

The length of the ceramic fiber was determined using an optical microscope (Olympus MX61, Tokyo, Japan) fit with a CCD Camera (Olympus DP72, Tokyo, Japan) and analytic software (Olympus Stream Essentials, Tokyo, Japan). Samples were prepared by spreading representative samplings of the ceramic fiber on a glass slide and measuring the lengths of at least 200 ceramic fibers at 10× magnification.

Average Surface Area—BET Gas Adsorption

Average surface area was measured using Brunauer-Emmitt-Teller (BET) gas adsorption. Use a Gemini V 2380 (Micromeritics, Norcross, Ga., USA) BET gas adsorption unit, which tests BET surface area using the static volumetric principle. The data was analyzed using Gemini V 2380 V1.00 software, which determines surface area using various thermodynamic models and using a molecular statistics model based on non-localized Density Function Theory. Samples were prepared by soaking for 2 hours at 350° C. under a dry $N_2$ gas purge.

Contrast Ratio (CR) Test Method

Samples of uncured composite material were formed into 1 mm thick by 30 mm diameter disks using a stainless steel mold. The formed samples were pressed flat in a Carver Press at 10,000 to 15,000 psi between sheets of mylar film. The disks were cured by exposing the disks to illumination from an LED array (455 nm wavelength, 850 mW/cm² intensity—Clear Stone Technology, Hopkins, Minn. USA: Control Unit CF2000, LED array JL2-455F-90) for 20 s on one side of the disk. ASTM-D2805-95 (Hiding Power of Paints by Reflectometry) was modified to measure a disk. The test method measures the CR or visual opacity of a material. Y-tristimulus values for the disks of cured composite material were measured on a Color i7 spectrophotometer (X-Rite, Grand Rapids, Mich., USA) with a 25 mm aperture using separate white and black backgrounds. All measurements were made in reflection mode with a D65 Illuminant with no filters. A 10 degree angle of view was used. CR was calculated as the ratio of the Y-tristimulus of a cured composite material on a black substrate to the Y-tristimulus through an identical material on a white substrate ($CR=R_B/R_W \times 100$) in reflectance. Lower CR values are indicative of more translucent materials.

Flexural Strength and Flexural Modulus Test Method

Test Specimen were prepared by extruding uncured composite material into a 2 mm×2 mm×25 mm quartz glass mold to form a test bar. The test bar of the composite material was cured in the quartz glass mold using two XL3000 dental cure lights (3M ESPE, St. Paul, Minn., USA). The exit window of one light was placed over the center of the test bar and cured for 20 s, then using the 2 lights in tandem, the exit windows of the lights were placed over the uncured ends of the test bar and simultaneously cured the bar for 20 s. The test bar was flipped and the cure protocol repeated. The cured test bar of the composite material was pushed out of the quartz glass mold. The cured test bars of the composite material were submerged for about 24 hr in 37° C. deionized water prior to testing.

Flexural Strength and Flexural Modulus of the cured test bars of the composite material were measured on an Instron tester (Instron 5944, Instron Corp., Canton, Mass., USA) according to ANSI/ADA (American National Standard/American Dental Association) specification No. 27 (1993) at a crosshead speed of 0.75 mm/min and a span of 20 mm. The results were reported in MPa for Flexural Strength and GPa for Flexural Modulus.

Fracture Toughness Test Method

Test Specimen were prepared by extruding uncured composite material into a 3 mm×5 mm×25 mm quartz glass mold to form a test bar. The test bar of the composite material was cured in the quartz glass mold using two XL3000 dental cure lights (3M ESPE, St. Paul, Minn., USA). The exit window of one light was placed over the center of the test bar and cured for 20 s, then using the 2 lights in tandem, the exit windows of the lights were placed over the uncured ends of the test bar and simultaneously cured the bar for 20 s. The test bar was flipped and the cure protocol repeated. The test bar of the cured composite material was pushed out of the quartz glass mold. Next, a notch was cut in the center of the test bar with a wafering blade with a kerf of 0.15 mm (Buehler, Lake Bluff, Ill., USA) using an ISOMET Low Speed Saw (Buehler, Lake Bluff, Ill., USA). The notch was approximately 2 mm deep. The cured test bars of the composite material were submerged for about 24 hr in 37° C. deionized water prior to testing.

Fracture Toughness was measured on an Instron tester (Instron 5944, Instron Corp., Canton Mass., USA) with a crosshead speed of 0.75 mm/min. The toughness was calculated per ASTM 399-05.

Gloss Retention after Toothbrush Abrasion Test Method

Samples of uncured composite were formed using a stainless steel mold into 2 mm thick×21 mm long×10 mm wide tiles. The uncured composite was pressed flat between sheets of polyester film in a Carver Press (Wabash, Ind., USA) at 6000 to 10,000 psi and cured for 20 s in LED array with 455 nm wavelength, 850 mW/cm² intensity (Clear Stone Technology, Hopkins, Minn., USA: Control Unit CF2000, LED array JL2-455F-90). The sample was removed from mold and polish to high gloss using an Ecomet 4 Variable Speed Grinder—Polisher fit with an Automet 2 Power Head (Buehler, Lake Bluff, Ill., USA). High gloss was achieved through the use of consecutively finer grinding and polishing media. First, 320 grit silicon carbide sandpaper was used followed by 600 grit silicon carbide sandpaper (sandpaper from 3M, St. Paul, Minn., USA). Next, 9 micrometer diamond paste was used followed by 3 micrometer paste, and finally 0.05 micrometer polishing slurry was used (polishing paste and slurry purchased from Buehler, Lake Bluff, Ill., USA). The tiles were stored for about 24 hrs submerged in 37° C. water.

The polish retention of the tiles was measured by challenging the polished surface by toothbrush abrasion. The tile was affixed in a jig, gloss side up. The initial gloss was measured (see "Sixty Degree Gloss"). The jig was placed in a well in an automated brushing machine where 5 ml of abrasive slurry consisting of 1 to 1 Crest Regular Toothpaste (P&G, Cincinnati, Ohio, USA) and water was placed over the tile. The tile was then brushed under a load of 450 gf with a 47 tuft Acclean toothbrush (Henry Schein, Melville, N.Y., USA). The tiles were subjected to 6000 total brush cycles, with the gloss measured every 1500 cycles. Five ml of fresh slurry were added after every gloss measurement.

Polishability Test Method

Tiles of the cured composite material were formed as discussed above for the Gloss Retention after Toothbrush Abrasion Test Method. The surface of the tile was uniformly roughened with 320 grit silicon carbide sand paper. The roughened surface was polished using a Sof-Lex™ Spiral Finishing Wheel and a Sof-Lex™ Spiral Polishing Wheel (3M ESPE St. Paul, Minn., USA). A mechanical arm was fit with a dental hand piece to provide constant motion and force (60 gf) for the Sof-Lex™ Spiral Finishing Wheel or the Sof-Lex™ Spiral Polishing Wheel. The roughened tiles were finished and polished for 1 min at 1500 rpm with each wheel. Sixty degree gloss of the surface of the cured composite was measured (see Sixty Degree Gloss) after the polishing step.

Materials

"BisEMA-6" refers to ethoxylated (6 mole ethylene oxide) bisphenol A dimethacrylate as further described in U.S. Pat. No. 6,030,606, available from Sartomer Co., Inc. (Exton, Pa.) as "CD541";

"BisGMA" refers to 2,2-bis[4-(2-hydroxy-3-methacryloyloxypropoxy)phenyl]propane (also referred to as bisphenol A diglycidyl ether methacrylate), CAS Reg. No. 1565-94-2.

"BHT" refers to butylated hydroxytoluene (2,6-di-tert-butyl-4-methylphenol), CAS Reg. No. 128-37-0;

"BZT" refers to 2-(2'-hydroxy-5'-methacryloxyethylphenyl)-2H-benzotriazole, CAS Reg. No. 96478-09-0, available from Ciba, Inc. (Tarrytown, N.Y.) as "TINUVIN R 796", also available from Sigma-Aldrich Corp. (St. Louis, Mo.);

"CPQ" refers to camphorquinone, CAS Reg. No. 10373-78-1;

"DPIHFP" or "DPIPF6" refers to diphenyliodonium hexafluorophosphate, CAS Reg. No. 58109-40-3, available from Johnson Matthey, Alfa Aesar Division (Ward Hill, Mass.);

"EDMAB" refers to ethyl 4-dimethylaminobenzoate, CAS Reg. No. 10287-53-3;

"ENMAP" refers to ethyl N-methyl-N-phenyl-3-aminopropionate (also referred to as N-methyl-N-phenyl-beta-alanine ethyl ester), CAS Reg. No. 2003-76-1, which can be prepared by known methods, such as those described by Adamson, et al.; JCSOA9; J. Chem. Soc.; 1949; spl. 144-152, which is incorporated herein by reference; also available from Johnson Matthey, Alfa Aesar Division (Ward Hill, Mass.);

"GENIOSIL GF-31" or "GF-31" refers to 3-methacryloxypropyltrimethoxysilane, available from Wacker Chemie AG (Munich, Germany);

"IRGACURE 819" refers to a bis(2,4,6-trimethylbenzoyl) phenylphosphine oxide photoinitiator, CAS Reg. No. 162881-26-7, available from Ciba Specialty Chemicals Corp. (Tarrytown, N.Y.), also available from Sigma-Aldrich Corp. (St. Louis, Mo.);

"PEG600 DM" refers to poly(ethylene glycol) dimethacrylate, average MW~600, obtained from Sartomer Co., Inc. (Exton, Pa.);

"PROCRYLAT" refers to 2,2-bis-4-(3-methacryloxypropoxy)phenyl)propane dimethacrylate, CAS Reg. No. 27689-12-9, as further described in WO2006/020760;

"TEGDMA" refers to triethyleneglycol dimethacrylate, CAS Reg. No. 109-16-0, available from Sartomer Co., Inc. (Exton, Pa.);

"UDMA" refers to diurethane dimethacrylate, CAS Reg. No. 72869-86-4, obtained under the trade designation "ROHAMERE 6661-0" from Rohm America LLC (Piscataway, N.J.); also available from Dajac Laboratories (Trevose, Pa.);

Fillers

"S/T Silica/Zirconia Nanoclusters" refers to silane-treated silica-zirconia nanocluster filler, prepared essentially as described in U.S. Pat. No. 6,730,156 at column 25, lines 50-63 (Preparatory Example A) and at column 25, line 64 through column 26, line 40 (Preparatory Example B) with minor modifications, including performing the silanization in 1-methoxy-2-propanol (rather than water) adjusted to a pH of about 8.8 with $NH_4OH$ (rather than to a pH of 3-3.3 with trifluoroacetic acid), and obtaining the S/T Silica/Zirconia Clusters by gap drying (rather than spray drying).

"S/T Zirconia/Silica Filler" refers to zirconia-silica filler (which can be prepared as described in U.S. Pat. No. 6,624,211 at column 15, line 60 through column 16, line 28) silane-treated in the following manner. Mix one hundred parts of the filler with deionized water at a solution temperature of between 20-30° C. Adjust the pH of the resulting slurry to 3-3.3 with trifluoroacetic acid (0.278 parts). Add 7 parts (based on the one hundred parts of the filler) of 3-methacryloxypropyltrimethoxysilane (available from Wacker Chemie AG, Munich, Germany) to the slurry. Mix the slurry for 2 hrs. At the end of 2 hrs, neutralize the pH of the slurry with calcium hydroxide. Recover the S/T Zirconia/Silica by drying, crushing and screening through a 74 micrometer screen.

"S/T 20 nm Silica Nanoparticle" refers to silane-treated silica nanoparticle filler having a nominal particle size of approximately 20 nanometers, prepared essentially as described in U.S. Pat. No. 6,572,693 at column 21, lines 63-67 (Nano-sized particle filler, Type #2);

"S/T Nanozirconia Nanoparticle" refers to silane-treated zirconia nanoparticle filler, which can be prepared from the zirconia sol as generally described in U.S. Pat. No. 8,647,510 at column 36 line 61 to column 37 line 16 (Example 11A-IER). The zirconia sol is added to an equivalent weight of 1-methoxy-2-propanol containing 3-methacryloxypropyltrimethoxysilane (1.1 mmol of 3-methacryloxypropyltrimethoxysilane per gram of nanozirconia to be surface treated). The mixture is heated to about 85° C. for 3 hours with stirring. The mixture is cooled to 35° C., adjusted to a pH of about 9.5 with $NH_4OH$, and the mixture reheated to about 85° C. for 4 hours with stirring. The resultant S/T Nanozirconia is isolated by removing solvents via gap drying. S/T Nanozirconia may also be prepared as described in U.S. Pat. No. 7,649,029 beginning at column 19, line 39 through column 20, line 41 (Filler I), except for the substitution of 3-methacryloxypropyltrimethoxysilane for the blend of Silquest A-174 and A-1230, and further removing the solvents via gap drying.

Ceramic Fiber

Ceramic Fiber 0

Amorphous aluminoborosilicate ceramic fibers with diameters of 10-12 µm (available from 3M Company as NEXTEL™ 312, approximate composite of 62.5% $Al_2O_3$, 24.5% $SiO_2$, 13% $B_2O_3$, Denier of 3,600 g/9,000 m, RI of 1.568) were chopped to a relatively narrow length distribution. The chopped ceramic fibers were heat treated at 700° C. in air for 1 to 4 hours to remove organic coatings to provide Ceramic Fiber 0.

Ceramic Fiber 0 had an average surface area of <0.5 $m^2/g$ as measured by BET gas adsorption. The ceramic fiber length, as discussed above in the detailed description, is giving by the fraction of the chopped ceramic fibers that are either less than or equal to than a given "L" ceramic fiber length value. As discussed herein, these values are denoted by "L" values (e.g., L10, L25, L50, L75, L90 and L99) where the number following the "L" indicates the percentage (based on a total number of the ceramic fibers) of the ceramic fibers (for a given number of ceramic fibers) that have a length that is either less than or equal to a given "L" length value.

For Ceramic Fiber 0, the L50 (median) length value was 147 µm, the L10 length value was 106 µm, the L25 length value was 131 µm, the L75 length value was 157 µm and the L90 length value was 168 µm.

Ceramic Fiber 1

Ceramic Fiber 0 (20.0017 g) was dispersed in a mixture of ethyl acetate (23.1 g), GF-31 (0.0213 g), and 30% aqueous ammonium hydroxide solution (0.54 g). The dispersion was stirred overnight at room temperature (23° C.). The ceramic fibers were then flash dried in a fume hood and heated to 80° C. for 30 minutes to provide Ceramic Fiber 1 (surface modified). The L10, L25, L50, L75, and L90 length values for Ceramic Fiber 1 were substantially the same as those listed for Ceramic Fiber 0.

Ceramic Fiber 2

Ceramic Fiber 2 were prepared in a fashion similar to Ceramic Fiber 1, except that prior to surface modification with GF-31, the ceramic fibers were subjected to a boiling water treatment as follows. The ceramic fibers (508 g) were dispersed in deionized water and boiled for 120 min. The boiled ceramic fibers were recovered by filtration and then dried. Analysis of the boiled ceramic fibers by BET gas adsorption indicated a surface area of about 23 $m^2/g$.

The boiled ceramic fibers (302.1 g) were dispersed in a mixture of ethyl acetate (399.2 g), GF-31 (6.8 g), and 30% aqueous ammonium hydroxide solution (6.0 g). The dispersion was stirred overnight at room temperature (23° C.). The ceramic fibers were flash dried in a fume hood and then heated to 80° C. for 30 minutes to provide Ceramic Fiber 2. The L10, L25, L50, L75, and L90 length values for Ceramic Fiber 2 were substantially the same as those listed for Ceramic Fiber 0.

Ceramic Fiber 3

Alumina ceramic fibers with diameters of 10-12 µm (available from 3M Company as NEXTEL™ 610, >99% α-$Al_2O_3$, Denier of 10,000 g/9,000 m, RI of 1.74) were chopped to a relatively narrow length distribution. The chopped ceramic fibers were heat cleaned at 700° C. in air for 1-4 hours to remove organic coatings to provide base ceramic fibers. The ceramic fibers had an average surface area of <0.2 $m^2/g$ taken from materials property sheet and an arithmetic mean length of 190 µm with a standard deviation of 30 µm according to SEM measurements provided by the ceramic fiber processor. The base ceramic fibers were silane treated as described for Ceramic Fiber 1 to provide Ceramic Fiber 3. For Ceramic Fiber 3, the L50 (median) length value was 130 µm, the L10 length value was 51 µm, the L25 length value was 79 µm, the L75 length value was 173 µm and the L90 length value was 220 µm.

Ceramic Fiber 4

Alumina-silica ceramic fibers with diameters of 10-12 µm (available from 3M Company as NEXTEL™ 720, approximately 85% $Al_2O_3$ and 15% $SiO_2$, Denier of 10,000 g/9,000 m) were chopped to a relatively narrow length distribution. The chopped ceramic fibers were heat cleaned at 700° C. in air for 1-4 hours to remove organic coatings to provide the base ceramic fibers. The base ceramic fibers had an average surface area of <0.2 $m^2/g$ taken from materials property sheet and an arithmetic mean length of 180 µm with a standard deviation of 40 µm according to SEM measurements provided by the ceramic fiber processor. The base ceramic fibers were silane treated as described for Ceramic Fiber 1 to provide Ceramic Fiber 4. For Ceramic Fiber 4, the L50 (median) length value was 163 µm, the L10 length value was 55 µm, the L25 length value was 132 µm, the L75 length value was 188 µm and the L90 length value was 207 µm.

Ceramic Fiber 5

Amorphous aluminoborosilicate ceramic fibers with diameters of 10-12 µm (available from 3M Company as NEXTEL™ 312, approximate composite of 62.5% $Al_2O_3$, 24.5% $SiO_2$, 13% $B_2O_3$, Denier of 3,600 g/9,000 m, RI of 1.568) were chopped to a relatively narrow length distribution. The chopped ceramic fibers were heat cleaned at 700° C. in air for 1-4 hours to remove organic coatings to provide Ceramic Fiber 5. Ceramic Fiber 5 had an average surface area of <0.2 $m^2/g$ taken from materials property sheet and an arithmetic mean length of 2950 µm with a standard deviation of 120 µm according to SEM measurements taken from Ceramic Fiber 5. Due to the large lengths for Ceramic Fiber 5, the L90 length value was assumed to be greater than 500 µm.

Ceramic Fiber 6

Ceramic Fiber 6 was formed by milling Ceramic Fiber 0 as follows. A small scale jar mill (Roalox Model 774, size 000, Gardco, a Paul N Gardner Company, Pompano Beach, Fla., USA) was filled with 400 g of ⅜" yttria stabilized zirconia rod milling media and 50.41 g of Ceramic Fiber 0, and the ceramic fibers milled for 2 hours at 250 rpm. The median ceramic fiber length of Ceramic Fiber 6 was 45 µm when measured with an optical microscope, the L10 value was 27 µm, the L25 value was 34 µm, the L75 value was 59 µm and the L90 value was 77 µm.

As more fully detailed below, the composite materials of the present disclosure include ceramic fibers as a filler material. The composite materials of the present disclosure display excellent handling characteristics. The cured composite materials of the present disclosure also display significant increases in mechanical performance (e.g., fracture toughness and flexural modulus among others) in comparison to cured composite materials that lack ceramic fiber filler altogether, or lacked a ceramic fiber filler with an appropriate length and/or length distribution. The increase in mechanical performance of the composite materials of the present disclosure may be particularly useful in dental applications, such as in the posterior regions of the mouth where there is a need for highly durable restorations. Additionally, the ceramic fibers of the composite materials of the present disclosure have refractive indices which can match the hardened polymerizable component of the composite system, thereby providing a composite material from which highly aesthetic restorations may be prepared. Finally, cured composite materials of the present disclosure provided excellent polishability and polish retention characteristics.

Composite Material

A first polymerizable component, Resin 1, was prepared by mixing the components shown in Table 1 at 45° C. until all of the components are uniformly mixed. Resin 1 was used to prepare composite materials with rheological properties similar to typical universal (sculptable) dental composites.

TABLE 1

| Polymerizable Component - Resin 1 | |
|---|---|
| Component | wt. % |
| BisGMA | 24.575% |
| TEGDMA | 1.182% |
| UDMA | 34.401% |
| BisEMA-6 | 34.401% |
| PEG600 DM | 3.736% |
| CPQ | 0.220% |
| DPIHFP | 0.350% |
| IRGACURE 819 | 0.050% |
| ENMAP | 0.810% |
| BHT | 0.150% |
| BZT | 0.125% |

A second polymerizable component, Resin 2, was prepared by mixing the components shown in Table 2 until all of the components are uniformly mixed. Resin 2 was used to prepare composite materials with rheological properties similar to typical flowable dental composites.

TABLE 2

| Polymerizable Component - Resin 2 | |
|---|---|
| Component | wt. % |
| BisGMA | 26.27% |
| TEGDMA | 15.76% |
| PROCRYLAT | 56.22% |
| CPQ | 0.16% |
| DPIHFP | 0.30% |
| EDMAB | 0.60% |
| BHT | 0.09% |
| BZT | 0.60% |

Examples of the composite materials were prepared by mixing the components shown in Table 3 until uniform. In all cases, the composite materials displayed acceptable handling characteristics.

TABLE 3

Composite Material Formulations for Universal (Sculptable) and Flowable Dental Composites Containing Varying Levels of Ceramic Fiber 0 and Nanoclusters

| Composite Material Example (Ex)/ Comparative Example (CE) | Resin 1 (wt. %) | Resin 2 (wt. %) | S/T Nano-zirconia NP[¶] (wt. %) | S/T 20 nm Silica NP[¶] (wt. %) | S/T Silica/ Zirconia Nano-clusters (wt. %) | S/T Zirconia/ Silica Filler (wt. %) | Ceramic Fiber 0 (wt. %) |
|---|---|---|---|---|---|---|---|
| CE A* (Paste 1) | 21.0 | 0.0 | 4.1 | 7.7 | 67.2 | 0.0 | 0.0 |
| EX 1* (Paste 2) | 21.0 | 0.0 | 3.9 | 7.4 | 63.7 | 0.0 | 4.0 |
| EX 2* (Paste 3) | 21.0 | 0.0 | 3.7 | 6.9 | 60.5 | 0.0 | 7.9 |
| EX 3* (Paste 4) | 21.0 | 0.0 | 3.3 | 6.2 | 53.7 | 0.0 | 15.8 |
| CE B* (Paste 5) | 21.0 | 0.0 | 0.0 | 0.0 | 0.0 | 79.0 | 0.0 |
| CE C* (Paste 6) | 21.0 | 0.0 | 0.0 | 0.0 | 0.0 | 71.1 | 7.9 |
| CE D[§] (Paste 7) | 0.0 | 35.0 | 0.0 | 7.2 | 57.8 | 0.0 | 0.0 |
| EX 4[§] (Paste 8) | 0.0 | 35.0 | 0.0 | 5.0 | 40.0 | 0.0 | 20.0 |
| EX 5[§] (Paste 9) | 0.0 | 35.0 | 0.0 | 2.8 | 22.2 | 0.0 | 40.0 |
| CE E[§] (Paste 10) | 0.0 | 35.0 | 0.0 | 0.0 | 0.0 | 65.0 | 0.0 |
| CE F[§] (Paste 11) | 0.0 | 35.0 | 0.0 | 0.0 | 0.0 | 45.0 | 20.0 |
| CE G[§] (Paste 12) | 0.0 | 35.0 | 0.0 | 0.0 | 0.0 | 25.0 | 40.0 |

*Universal (sculptable) formulations
[§]Flowable formulations
[¶]NP- Nanoparticle The above identified composite materials (Table 3) were cured according to the methods described above and subjected to mechanical testing to evaluate the properties of the materials made with varying levels of Ceramic Fiber 0 and nanoclusters. Mechanical testing data is summarized in Table 4, below.

TABLE 4

Fracture Toughness, Flexural Strength, Flexural Modulus, and Polish Retention Data for Selected Cured Composite Materials

| Example (EX) and Comparative Example (CE) | Nano-cluster filler? | Ceramic Fiber 0 (wt. %) | Fracture Toughness, $MPa \cdot m^{0.5}$ (Std. Dev.) | Flexural Strength MPa (Std. Dev.) | Flexural Modulus, GPa (Std. Dev.) | Polish Retention 60° gloss unit (Std. Dev.) |
|---|---|---|---|---|---|---|
| CE A*  | Yes | 0    | 2.09 (0.11) | 152.8 (7.4)  | 12.2 (0.3) | 76.1 (1.5) |
| EX 1*  | Yes | 4.0  | 2.29 (0.14) | 149.7 (10.9) | 13.7 (0.3) | Not tested |
| EX 2*  | Yes | 7.9  | 2.41 (0.11) | 159.3 (6.2)  | 14.9 (0.4) | 63.7 (2.1) |
| EX 3*  | Yes | 15.8 | 2.66 (0.11) | 172.2 (10.3) | 17.2 (0.2) | 59.2 (2.3) |
| CE B*  | No  | 0    | 2.32 (0.22) | 161.2 (5.0)  | 11.5 (0.4) | 8.2 (0.3)  |
| CE C*  | No  | 7.9  | 2.70 (0.17) | 164.0 (11.0) | 13.9 (0.3) | 10.3 (0.4) |
| CE D§ | Yes | 0    | Not tested  | 130.5 (7.9)  | 8.2 (0.2)  | Not tested |
| EX 4§ | Yes | 20   | Not tested  | 139.3 (7.2)  | 13.0 (0.4) | Not tested |
| EX 5§ | Yes | 40   | Not tested  | 143.5 (5.4)  | 17.2 (0.5) | Not tested |
| CE E§ | No  | 0    | Not tested  | 144.5 (10.7) | 7.9 (0.2)  | Not tested |
| CE F§ | No  | 20   | Not tested  | 130.3 (7.9)  | 12.9 (0.2) | Not tested |
| CE G§ | No  | 40   | Not tested  | 120.7 (3.3)  | 16.9 (0.6) | Not tested |

*Univeral (sculptable) formulations
§Flowable formulations

As seen in Table 4, the addition of Ceramic Fiber 0 increases the fracture toughness and flexural modulus of the cured composite material (cf. CE A and EX 1), where the more Ceramic Fiber 0 that is added to the composition the larger the gain (cf. EX 1 and EX 3). While ceramic fibers such as Ceramic Fiber 0 provided cured composites with improved mechanical properties, formulations which lacked nanocluster filler provided cured composites with poor polish retention properties (cf. EX 2 and CE C). Table 4 also shows that incorporation of Ceramic Fiber 0 into flowable composite formulations provides cured materials with improved flexural modulus properties, nearing those of universal (sculptable) composites (cf. EX 5 and EX 3). This gives rise to the potential for expanded indications of flowable composite materials.

Impact of Ceramic Fiber Treatments

TABLE 5

Composite Material Formulations for Universal (Sculptable) and Flowable Dental Composites Containing Varying Levels of Ceramic Fiber 0, Ceramic Fiber 1 (Surface Treated), or Ceramic Fiber 2 (Surface Treated After Boiling)

| Composite Material Example (Ex)/ Comparative Example (CE) | Resin 1 (wt. %) | Resin 2 (wt. %) | S/T Nano-Zirconia NP$^\eta$ (wt. %) | S/T 20 nm Silica NP$^\eta$ (wt. %) | S/T Silica/ Zirconia Nano-cluster (wt. %) | S/T Zirconia/ Silica Filler (wt. %) | Ceramic Fiber 0 (wt. %) | Ceramic Fiber 1 (wt. %) | Ceramic Fiber 2 (wt. %) |
|---|---|---|---|---|---|---|---|---|---|
| CE A* (Paste 1)  | 21.0 | 0.0  | 4.1 | 7.7 | 67.2 | 0.0 | 0.0  | 0.0  | 0.0  |
| EX 3* (Paste 4)  | 21.0 | 0.0  | 3.3 | 6.2 | 53.7 | 0.0 | 15.8 | 0.0  | 0.0  |
| EX 6* (Paste 13) | 22.0 | 0.0  | 4.1 | 7.6 | 50.7 | 0.0 | 0.0  | 15.6 | 0.0  |
| EX 7* (Paste 14) | 21.0 | 0.0  | 3.3 | 6.2 | 53.7 | 0.0 | 0.0  | 0.0  | 15.8 |
| CE D§ (Paste 7) | 0.0  | 35.0 | 0.0 | 7.2 | 57.8 | 0.0 | 0.0  | 0.0  | 0.0  |
| EX 5§ (Paste 9) | 0.0  | 35.0 | 0.0 | 2.8 | 22.2 | 0.0 | 40.0 | 0.0  | 0.0  |
| EX 8§ (Paste 15)| 0.0  | 35.0 | 0.0 | 2.8 | 22.2 | 0.0 | 0.0  | 0.0  | 40.0 |

TABLE 5-continued

Composite Material Formulations for Universal (Sculptable) and Flowable Dental Composites Containing Varying Levels of Ceramic Fiber 0, Ceramic Fiber 1 (Surface Treated), or Ceramic Fiber 2 (Surface Treated After Boiling)

| Composite Material Example (Ex)/ Comparative Example (CE) | Resin 1 (wt. %) | Resin 2 (wt. %) | S/T Nano-Zirconia NP^η (wt. %) | S/T 20 nm Silica NP^η (wt. %) | S/T Silica/Zirconia Nano-cluster (wt. %) | S/T Zirconia/Silica Filler (wt. %) | Ceramic Fiber 0 (wt. %) | Ceramic Fiber 1 (wt. %) | Ceramic Fiber 2 (wt. %) |
|---|---|---|---|---|---|---|---|---|---|
| CE E§ (Paste 10) | 0.0 | 35.0 | 0.0 | 0.0 | 0.0 | 65.0 | 0.0 | 0.0 | 0.0 |
| CE G§ (Paste 12) | 0.0 | 35.0 | 0.0 | 0.0 | 0.0 | 25.0 | 40.0 | 0.0 | 0.0 |
| CE H§ (Paste 16) | 0.0 | 35.0 | 0.0 | 0.0 | 0.0 | 25.0 | 0.0 | 0.0 | 40.0 |

*Universal (sculptable) formulations
§Flowable formulations
^ηNP-Nanoparticle

The above identified composite materials (Table 5) were cured according to the methods described above and subjected to mechanical testing to evaluate the properties of the materials made with varying levels and types of chopped ceramic fibers. Mechanical testing data is summarized in Table 6, below.

TABLE 6

Flexural Strength Data for Selected Cured Composite Materials - Impact of Surface Treatment of the Ceramic Fiber

| Example (EX) and Comparative Example (CE) | Nanocluster filler? | Ceramic fiber (wt. %) | Flexural Strength MPa (Std. Dev.) |
|---|---|---|---|
| EX 1* (Paste 2) | Yes | 15.8 (Ceramic Fiber 0) | 171.9 (8.9) |
| EX 7* (Paste 14) | Yes | 15.8 Ceramic Fiber 2 | 181.9 (3.1) |
| EX 6* (Paste 13) | Yes | 15.6 (Ceramic Fiber 1) | 183.7 (5.3) |
| EX 5§ (Paste 9) | Yes | 40 (Ceramic Fiber 0) | 143.5 (5.4) |
| CE G§ (Paste 12) | No | 40 (Ceramic Fiber 0) | 120.7 (3.3) |
| EX 8§ (Paste 15) | Yes | 40 (Ceramic Fiber 2) | 193.3 (17.1) |
| CE H§ (Paste 16) | No | 40 (Ceramic Fiber 2) | 196.5 (9.4) |

*Univeral (sculptable) formulations
§Flowable formulations

The data in Table 6 demonstrates how fiber treatment impacts the flexural strength on the resultant cured composite. In the case of universal composite formulations, flexural strength improved with silane surface treatment of the ceramic fiber (i.e., EX 6 or EX 7 in comparison to EX 1). Similarly, the flexural strength of cured flowable composite formulations also improved (i.e., EX 8 or CE H in comparison to EX 5 or CE G).

Impact of Fiber-Filler-Resin Load

TABLE 7

Composite Material Formulations for Universal (Sculptable) and Flowable Dental Composites Containing Varying Levels of Ceramic Fiber Ceramic Fiber 2 and Silica/Zirconia Nanoclusters or Zirconia/Silica Filler

| Composite Material Example (Ex)/ Comparative Example (CE) | Resin 1 (wt. %) | Resin 2 (wt. %) | S/T Nano-zirconia NP^η (wt.%) | S/T 20 nm Silica NP^η (wt. %) | S/T Silica/Zirconia Nano-clusters (wt. %) | S/T Zirconia/Silica Filler (wt. %) | Ceramic Fiber 2 (wt. %) | Ceramic Fiber 0 (wt. %) |
|---|---|---|---|---|---|---|---|---|
| CE B* (Paste 5) | 21.0 | 0.0 | 0.0 | 0.0 | 0.0 | 79.0 | 0.0 | 0.0 |
| CE C* (Paste 6) | 21.0 | 0.0 | 0.0 | 0.0 | 0.0 | 71.1 | 0.0 | 7.9 |
| CE A* (Paste 1) | 21.0 | 0.0 | 4.1 | 7.7 | 67.2 | 0.0 | 0.0 | 0.0 |
| CE L* | 20.0 | 0.0 | 3.5 | 6.5 | 70.0 | 0.0 | 0.0 | 0.0 |
| CE M* | 20.0 | 0.0 | 3.33 | 6.17 | 70.0 | 0.0 | 0.5 | 0.0 |

TABLE 7-continued

Composite Material Formulations for Universal (Sculptable) and
Flowable Dental Composites Containing Varying Levels of Ceramic Fiber
Ceramic Fiber 2 and Silica/Zirconia Nanoclusters or Zirconia/Silica Filler

| Composite Material Example (Ex)/ Comparative Example (CE) | Resin 1 (wt. %) | Resin 2 (wt. %) | S/T Nano-zirconia NP[π] (wt.%) | S/T 20 nm Silica NP[π] (wt. %) | S/T Silica/Zirconia Nano-clusters (wt. %) | S/T Zirconia/Silica Filler (wt. %) | Ceramic Fiber 2 (wt. %) | Ceramic Fiber 0 (wt. %) |
|---|---|---|---|---|---|---|---|---|
| CE N* | 20.0 | 0.0 | 2.45 | 4.55 | 70.0 | 0.0 | 3.0 | 0.0 |
| EX 1* (Paste 2) | 21.0 | 0.0 | 3.9 | 7.4 | 63.7 | 0.0 | 0.0 | 4.0 |
| EX 13* | 20.0 | 0.0 | 1.75 | 3.25 | 70.0 | 0.0 | 5.0 | 0.0 |
| EX 14* | 25.0 | 0.0 | 1.75 | 3.25 | 20.0 | 0.0 | 50.0 | 0.0 |
| EX 15* | 20.0 | 0.0 | 3.5 | 6.5 | 20.0 | 0.0 | 50.0 | 0.0 |
| CE O[§] | 0.0 | 35.0 | 4.9 | 4.9 | 55.2 | 0.0 | 0.0 | 0.0 |
| CE P[§] | 0.0 | 35.0 | 0.0 | 0.0 | 10.0 | 0.0 | 55.0 | — |
| EX 16[§] | 0.0 | 40.0 | 5.35 | 5.35 | 42.9 | 0.0 | 6.4 | 0.0 |
| EX 17[§] | 0.0 | 40.0 | 0.0 | 0.0 | 17.1 | 0.0 | 42.9 | 0.0 |
| EX 18[§] | 0.0 | 30.0 | 0.0 | 0.0 | 60.9 | 0.0 | 9.1 | 0.0 |
| EX 19[§] | 0.0 | 30.0 | 2.3 | 2.3 | 18.7 | 0.0 | 46.7 | 0.0 |
| EX 20[§] | 0.0 | 35.0 | 1.65 | 1.65 | 26.5 | 0.0 | 35.2 | 0.0 |
| EX 21[§] | 0.0 | 30.0 | 0.0 | 0.0 | 20.0 | 0.0 | 50.0 | 0.0 |

[π]NP-Nanonarticle

TABLE 8

Flexural Strength, Flexural Modulus, and Polish Retention Data for Selected Cured Composite Materials

| Example (EX) and Comparative Example (CE) | Nano-cluster filler? | Ceramic Fiber 0 (F0) or Ceramic Fiber 2 (F2) (wt. %) | Fracture Toughness, MPa · m^0.5 (Std. Dev.) | Flexural Strength MPa (Std. Dev.) | Flexural Modulus, GPa (Std. Dev.) | Polish Retention 60° gloss unit (Std. Dev.) |
|---|---|---|---|---|---|---|
| CE B* | No | F0 (0.0) | 2.32 (0.22) | 161.2 (5.0) | 11.5 (0.4) | 8.2 (0.3) |
| CE C* | No | F0 (7.9) | 2.70 (0.17) | 164.0 (11.0) | 13.9 (0.3) | 10.3 (0.4) |
| CE A* | Yes | F2 (0.0) | 2.09 (0.11) | 152.8 (7.4) | 12.2 (0.3) | 76.1 (1.5) |
| CE L* | Yes | F2 (0.0) | 2.04 (0.18) | 129.4 (8.7) | 10.3 (0.2) | Not Tested |
| CE M* | Yes | F2 (0.5) | 2.15 (0.04) | 132.2 (12.3) | 11.7 (0.9) | Not Tested |
| CE N* | Yes | F2 (3.0) | 2.00 (0.22) | 131.4 (3.5) | 11.6 (0.3) | 50.9 (4.9) |
| EX 1* | Yes | F0 (4.0) | 2.29 (0.14) | 149.7 (10.9) | 13.7 (0.3) | Not Tested |
| EX 13* | Yes | F2 (5.0) | Not Tested | 136.1 (3.4) | 12.6 (0.2) | Not Tested |
| EX 14* | Yes | F2 (50.0) | 2.91 (0.17) | 135.4 (16.2) | 16.4 (1.2) | 30.3 (2.2) |
| EX 15* | Yes | F2 (50.0) | 3.22 (0.20) | 125.6 (16.7) | 19.2 (1.5) | Not Tested |
| CE O[§] | Yes | F2 (0.0) | 1.49 (0.10) | 126.4 (9.0) | 7.9 (0.1) | 53.2 (8.2) |
| CE P[§] | Yes | F2 (55.0) | Not Tested | | | |
| EX 16[§] | Yes | F2 (6.4) | 1.62 (0.09) | 125.3 (8.2) | 8.2 (0.1) | 55.9 (3.4) |
| EX 17[§] | Yes | F2 (42.9) | 2.19 (0.23) | 179.0 (11.4) | 14.6 (0.4) | 36.0 (8.0) |
| EX 18[§] | Yes | F2 (9.1) | 1.74 (0.05) | 136.6 (11.7) | 11.7 (0.3) | 44.8 (5.6) |
| EX 19[§] | Yes | F2 (46.7) | Not Tested | 138.3 (15.4) | 15.4 (0.6) | 24.6 (2.2) |
| EX 20[§] | Yes | F2 (35.2) | Not Tested | 185.4 (15.2) | 15.2 (0.3) | 37.2 (3.8) |
| EX 21[§] | Yes | F2 (50) | Not Tested | 92.1 (12.8) | 16.4 (1.2) | Not Tested |

*Univeral (sculptable) formulations
[§]Flowable formulations

Impact of Ceramic Fiber Length

The length of the ceramic fiber impacts its efficacy at improving mechanical properties. Table 9 describes the composite material formulations containing blends of different ceramic fiber lengths (and length distributions). EX 3 contained Ceramic Fiber 0 only (a relatively short-chopped fiber with a narrow length distribution), CE K contained Ceramic Fiber 5 only (a relatively long-chopped fiber with a narrow length distribution), while CE I and CE J contained blends of Ceramic Fiber 0 and Ceramic Fiber 6. Ceramic Fiber 0, Ceramic Fiber 5, and Ceramic Fiber 6 were compositionally identical and lacked surface treatment. Table 10a describes the ceramic fiber length distributions, while Table 10b describes impact of fiber lengths and length distributions on flexural strength and modulus, as well as fracture toughness.

TABLE 9

Composite Material Formulations Containing Different Ceramic fiber Lengths

| Example (EX) and Comparative Example (CE) | Resin 1 (wt. %) | S/T Nano-zirconia Nanoparticle (wt. %) | S/T 20 nm Silica NP[a] (wt. %) | S/T Silica/Zirconia Nano-clusters (wt. %) | Ceramic Fiber 0 (wt. %) | Ceramic Fiber 6 (wt. %) | Ceramic Fiber 5 (wt. %) |
|---|---|---|---|---|---|---|---|
| EX 3 | 21.0 | 3.3 | 6.2 | 53.7 | 15.8 | 0.0 | 0.0 |
| EX 9 | 21.0 | 3.3 | 6.2 | 53.7 | 11.85 | 3.95 | 0.0 |
| CE I | 21.0 | 3.3 | 6.2 | 53.7 | 3.95 | 11.85 | 0.0 |
| CE J | 21.0 | 3.3 | 6.2 | 53.7 | 0.0 | 15.8 | 0.0 |
| CE K* | 21.0 | 3.3 | 6.2 | 53.7 | 0.0 | 0.0 | 15.8 |

[a]NP-Nanoparticle
*Ceramic Fiber 5 could not be dispersed in Resin 1 to provide CE K a homogeneous paste (unacceptable clumping). Mechanical properties of the cured composite were not tested.

TABLE 10a

Ceramic Fiber Length Impact on Properties

|  | EX 3 Ceramic fiber length (μm) | EX 9 Ceramic fiber length (μm) | CE I Ceramic fiber length (μm) | CE J Ceramic fiber length (μm) |
|---|---|---|---|---|
| L5 | 53.34 | 16.54 | 17.28 | 23.35 |
| L10 | 105.86 | 21.08 | 20.58 | 26.64 |
| L15 | 119.73 | 24.52 | 23.36 | 29.70 |
| L20 | 125.95 | 27.40 | 25.90 | 31.79 |
| L25 | 131.45 | 30.80 | 28.67 | 33.91 |
| L30 | 136.13 | 33.93 | 31.18 | 36.36 |
| L35 | 139.24 | 36.99 | 33.43 | 38.45 |
| L40 | 141.47 | 41.83 | 35.95 | 40.15 |
| L45 | 144.32 | 45.46 | 38.10 | 42.64 |
| L50 | 146.53 | 51.65 | 40.33 | 44.70 |
| L55 | 148.33 | 60.72 | 43.72 | 46.98 |
| L60 | 150.13 | 84.14 | 46.97 | 49.70 |
| L65 | 152.15 | 117.14 | 49.66 | 52.21 |
| L70 | 154.48 | 133.17 | 55.18 | 55.79 |
| L75 | 157.10 | 139.57 | 61.10 | 59.27 |
| L80 | 159.70 | 147.26 | 69.01 | 63.66 |
| L85 | 163.28 | 151.22 | 99.23 | 68.66 |
| L90 | 168.06 | 156.83 | 137.07 | 76.96 |
| L95 | 178.39 | 165.37 | 154.32 | 95.77 |
| L99 | 288.61 | 186.03 | 170.09 | 137.82 |

TABLE 10b

Ceramic Fiber Length Distribution Impact on Mechanical Properties

| Example (EX) and Comparative Example (CE) | Flexural Strength MPa (Std. Dev.) | Flexural Modulus, GPa (Std. Dev.) | Fracture Toughness, MPa · m^0.5 (Std. Dev.) |
|---|---|---|---|
| EX 3 | 172.2 (10.3) | 17.2 (0.2) | 2.7 (0.12) |
| EX 9 | 170.2 (3.9) | 16.7 (0.2) | 2.6 (0.17) |
| CE I | 153.3 (3.7) | 14.5 (0.3) | 2.5 (0.05) |
| CE J | 152.2 (6.9) | 14.2 (0.1) | 2.3 (0.14) |

As can be seen from Tables 10a and 10b, composite materials containing ceramic fiber with an L50 of about greater than 50 micrometers and an L75 of greater than about 130 micrometers yield superior mechanical properties.

Impact of Ceramic Fiber Composition

TABLE 11

Composite Material Formulations Containing Different Ceramic fiber Compositions

| Composite Material | Resin 1 (wt. %) | S/T Nano-zirconia Nanoparticle (wt. %) | S/T 20 nm Silica NP[a] (wt. %) | S/T Silica/Zirconia Nano-clusters (wt. %) | Ceramic Fiber 2 (wt. %) | Ceramic Fiber 3 wt % | Ceramic Fiber 4 wt % |
|---|---|---|---|---|---|---|---|
| Paste 21 | 21.5 | 4.1 | 7.7 | 51.0 | 15.7 | 0.0 | 0.0 |
| Paste 22 | 21.5 | 4.1 | 7.7 | 51.0 | 0.0 | 0.0 | 15.7 |
| Paste 23 | 21.5 | 4.1 | 7.7 | 51.0 | 0.0 | 15.7 | 0.0 |

[a]NP-Nanoparticle

In addition to improvements in mechanical properties, it is also desirable for the cured composite materials to polish to a high initial gloss using tools standard to the dental industry. To test this, polish select cured composite materials according to the Polishability Test Method. After polishing, measure the sixty degree gloss. Table 10 summarizes the initial gloss results for cured composite materials of EX 10, EX 11 and EX 12.

TABLE 12

Initial Gloss After Polishing for Cured Composite Materials

| Example (EX) | Gloss (60° gloss) |
|---|---|
| EX 10 (Paste 21) | 59.2 (2.0) |
| EX 12 (Paste 22) | 57.8 (0.1) |
| EX 11 (Paste 23) | 37.5 (0.8) |

As seen in Table 10, cured composite materials containing aluminoborosilicate ceramic fibers (EX 10) or alumina-silica ceramic fibers (EX 12) polish to a higher initial gloss than cured composite materials containing alumina ceramic fibers (EX 11). The initial 60° gloss obtained for EX 10 and EX 12 were particularly good, and approached that of a commercially available dental composite material (FILTEK Supreme Ultra Universal Restorative available from 3M ESPE, St. Paul, Minn.).

Each of the Ceramic fiber and the cured composite materials have a refractive index, where if the refractive index values of these two components match closely then the presence of the Ceramic fiber in the cured composite materials is less noticeable. The refractive index match can be demonstrated by measuring the contrast ratio of the cured composite material. As the contrast ratio is a measure of optical opacity, the lower the contrast ratio the more light transmits through the cured composite material. A desirable contrast ratio value for dental applications for unpigmented or deep curing is typically a value of about 55 or less. This allows for additional shading if desired.

The contrast ratio of EX 10, EX 11 and EX 12 were measured as described above in Contrast Ratio (CR) Test Method. Table 13 shows the results.

TABLE 13

Contrast Ratios Data for Cured Composite Materials

| Example | Contrast Ratio |
|---|---|
| EX 10 (Paste 21) | 41.7 |
| EX 12 (Paste 22) | 54.2 |
| EX 11 (Paste 23) | 67.6 |

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein. The complete disclosures of the patents, patent documents, and publications cited herein are incorporated by reference in their entirety as if each were individually incorporated.

We claim:

1. A composite material, comprising:
   20 to 40 weight percent (wt. %) of a polymerizable component;
   4 to 50 wt. % of ceramic fibers; and
   20 to 70 wt. % of nanoclusters, where the wt. % values of the composite material are based on a total weight of the composite material and total to a value of 100 wt. %, and where each of the ceramic fibers has a length and where the length of fifty percent of the ceramic fibers, based on a total number of the ceramic fibers, is at least 50 micrometers and the length of ninety percent of the ceramic fibers, based on the total number of the ceramic fibers, is no greater than 500 micrometers.

2. The composite material of claim 1, where the composite material includes up to 12 wt. % of nanoparticles.

3. The composite material of claim 2, where the composite material includes 2 to 12 wt. % of nanoparticles.

4. The composite material of claim 3, where the nanoparticles are discrete non-fumed metal oxide nanoparticles.

5. The composite material of claim 4, where the discrete non-fumed metal oxide nanoparticles are discrete non-fumed heavy metal oxide nanoparticles.

6. The composite material of claim 4, where the discrete non-fumed metal oxide nanoparticles include both discrete non-fumed heavy metal oxide nanoparticles and discrete non-fumed non-heavy metal oxide nanoparticles.

7. The composite material of claim 1, where the composite material includes 22 to 64 wt. % of nanoclusters.

8. The composite material of claim 1, where the ceramic fibers are at least partially amorphous ceramic fibers.

9. The composite material of claim 8, where the ceramic fibers are completely amorphous ceramic fibers.

10. The composite material of claim 1, where the composite material includes 4 to 40 wt. % of the ceramic fibers based on the total weight of the composite material.

11. The composite material of claim 1, where the length of sixty-five percent of the ceramic fibers, based on a total number of the ceramic fibers, is at least 100 micrometers and the length of ninety percent of the ceramic fibers, based on the total number of the ceramic fibers, is no greater than 350 micrometers.

12. The composite material of claim 1, where the ceramic fibers have an arithmetic mean length of 100 micrometers to 170 micrometers.

13. The composite material of claim 1, where the ceramic fibers have an arithmetic mean diameter of 0.5 to 20 micrometers.

14. The composite material of claim 13, where the arithmetic mean diameter of the ceramic fibers is 9 to 12 micrometers.

15. The composite material of claim 1, where an aspect ratio of a median length of the fifty percent of the ceramic fibers that are at least 50 micrometers to a median diameter of the fifty percent of the ceramic fibers that are at least 50 micrometers is at least 5:1 (median length:median diameter).

16. The composite material of claim 1, where the ceramic fibers are formed with aluminum oxide and silicon dioxide and have 14 weight percent or less of boron trioxide based on the total weight of the ceramic fibers.

17. The composite material of claim 1, where the ceramic fibers have a surface area of at least 10 square meters per gram ($m^2/g$).

18. The composite material of claim 1, where the polymerizable component forms a hardened polymerizable component having a refractive index, where the ceramic fibers have a refractive index value within 0.1 or less of the refractive index of the hardened polymerizable component.

19. The composite material of claim 18, where the ceramic fibers have a refractive index value within 0.05 or less of the refractive index of the hardened polymerizable component.

20. The composite material of claim 1, where the ceramic fibers have a refractive index value of 1.40 to 1.65.

21. The composite material of claim 20, where the refractive index value of the ceramic fibers is 1.50 to 1.58.

22. The composite material of claim 1, wherein the polymerizable component is an ethylenically unsaturated compound.

23. The composite material of claim 1, further including an initiator selected from the group consisting of a free radical initiator, a photoinitiator, a thermally activated initiator or a combination thereof.

24. The composite material of claim 1, further including a coupling agent, where the coupling agent provides a chemical bond between the ceramic fibers and the polymerizable component.

25. The composite material of claim 24, where the coupling agent is selected from the group consisting of an organosilane coupling agent, a titanate coupling agent, a zirconate coupling agent, an acidic coupling agent or a combination thereof.

26. The composite material of claim 1, where the composite material is hardened to become any one of a dental restorative, a dental adhesive, a dental mill blank, a dental cement, a dental prostheses, an orthodontic device, an orthodontic adhesive, a dental casting material or a dental coating.

27. The composite material of claim 1, where the nanoclusters are silica-zirconia nanoclusters.

28. The composite material of claim 27, where the silica-zirconia nanoclusters are formed by primary particles, where each of the primary particles has a diameter of 1 nanometer to 200 nanometers.

* * * * *